United States Patent
Garneau-Tsodikova et al.

(10) Patent No.: US 11,103,504 B2
(45) Date of Patent: Aug. 31, 2021

(54) COMBINATION OF A DNA CONDENSATION-INDUCING COMPOUND AND AN EIS INHIBITOR FOR ANTIBIOTIC TREATMENT

(71) Applicants: University of Kentucky Research Foundation, Lexington, KY (US); Academisch Medisch Centrum, Amsterdam (NL)

(72) Inventors: Sylvie Garneau-Tsodikova, Lexington, KY (US); Nicole Neeltje van der Wel, Amsterdam (NL)

(73) Assignees: University of Kentucky Research Foundation, Lexington, KY (US); Academisch Medisch Centrum, Amsterdam (NL)

( * ) Notice: Subject to any disclaimer, the term of this patent is extended or adjusted under 35 U.S.C. 154(b) by 0 days.

(21) Appl. No.: 16/518,736

(22) Filed: Jul. 22, 2019

(65) Prior Publication Data

US 2020/0022978 A1 Jan. 23, 2020

Related U.S. Application Data

(60) Provisional application No. 62/701,373, filed on Jul. 20, 2018.

(51) Int. Cl.
| | |
|---|---|
| *A61K 31/4985* | (2006.01) |
| *A61K 31/575* | (2006.01) |
| *A61K 31/4375* | (2006.01) |
| *A61K 31/7036* | (2006.01) |
| *A61K 31/496* | (2006.01) |
| *A61K 31/5377* | (2006.01) |
| *A61P 31/06* | (2006.01) |

(52) U.S. Cl.
CPC ...... *A61K 31/4985* (2013.01); *A61K 31/4375* (2013.01); *A61K 31/496* (2013.01); *A61K 31/5377* (2013.01); *A61K 31/575* (2013.01); *A61K 31/7036* (2013.01); *A61P 31/06* (2018.01)

(58) Field of Classification Search
CPC .............. A61K 31/4985; A61K 31/575; A61K 31/4375; A61K 31/7036; A61K 31/496; A61K 31/5377; A61P 31/06
See application file for complete search history.

(56) References Cited

PUBLICATIONS

Garzan, A.,"Sulfonamide-based inhibitors of aminoglycoside acetyltransferase Eis abolish resistance to kanamycin in *Mycobacterium tuberculosis*." Journal of medicinal chemistry 59.23 (2016): 10619-10628.*

Sakatos, A., Ph.D. Dissertation 2016; Harvard University; http://nrs.harvard.edu/urn-3:HUL.InstRepos:33493309 p. 1-92.*

Zusman, D. R., "Nucleoid condensation and cell division in *Escherichia coli* MX74T2 ts52 after inhibition of protein synthesis." Journal of bacteriology 115.3 (1973): 1167-1178.*

Scutigliani, et al., Interfering with DNA decondensation as a strategy against mycobacteria. Frontiers Microbiol., (2018), 9, 2034, pp. 1-12.

Garzan, et al., Combating Enhanced Intracellular Survival (Eis)-Mediated Kanamycin Resistance of *Mycobacterium tuberculosis* by Novel Pyrrolo[1,5-a]pyrazine-Based Eis Inhibitors. ACS infectious diseases (2017), 3, 302-309.

* cited by examiner

*Primary Examiner* — John M Mauro
(74) *Attorney, Agent, or Firm* — Stites & Harbison PLLC; Sean P. Ritchie

(57) ABSTRACT

A method of killing bacteria and an antibiotic kit are provided herein. The method includes treating the bacteria with a DNA condensation-inducing compound; and subsequently treating the bacteria with an Eis inhibitor. The kit includes a DNA condensation-inducing compound packaged together with an Eis inhibitor.

20 Claims, 13 Drawing Sheets

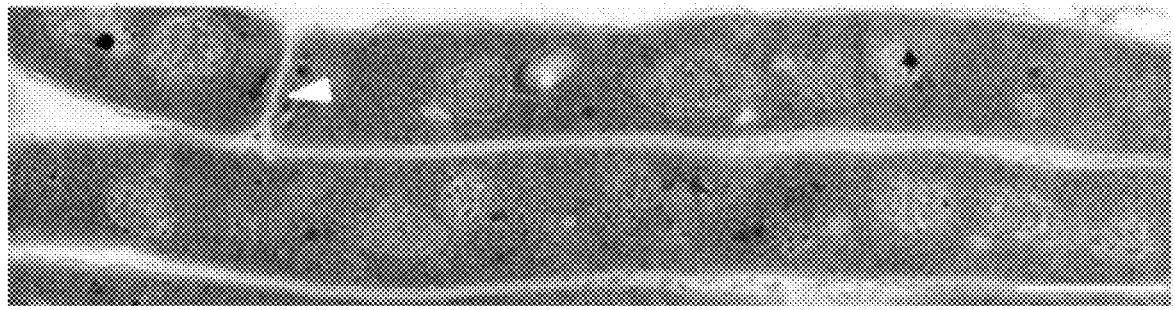
FIG. 1A
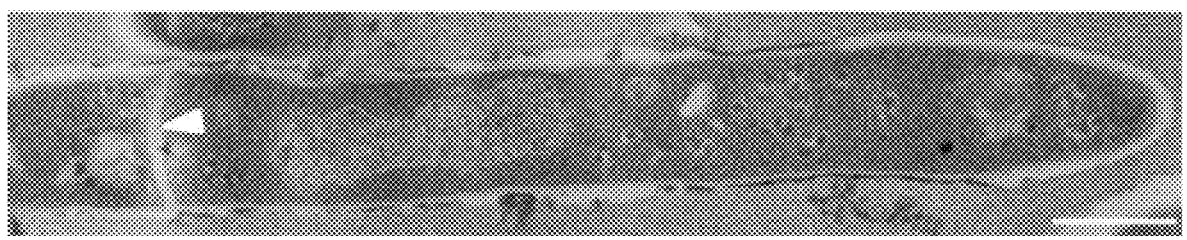
FIG. 1B
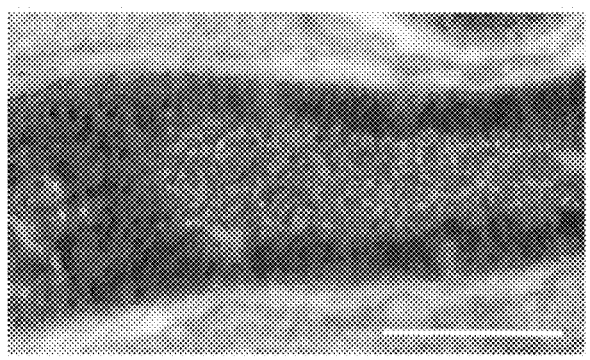 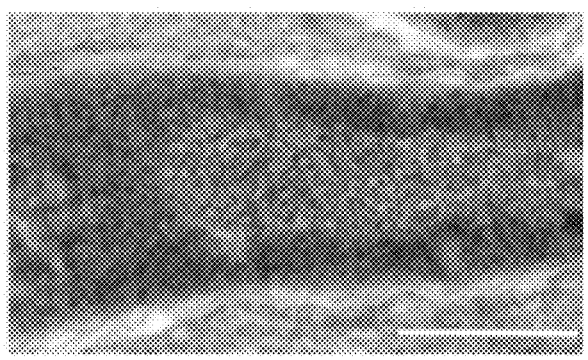
FIG. 1C  FIG. 1D

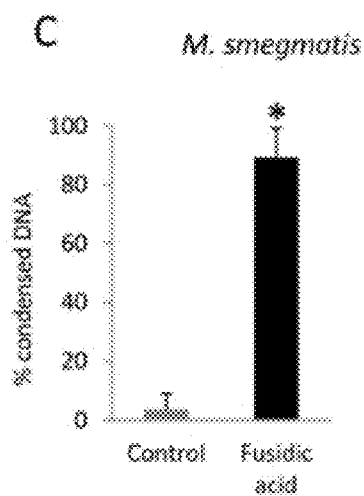 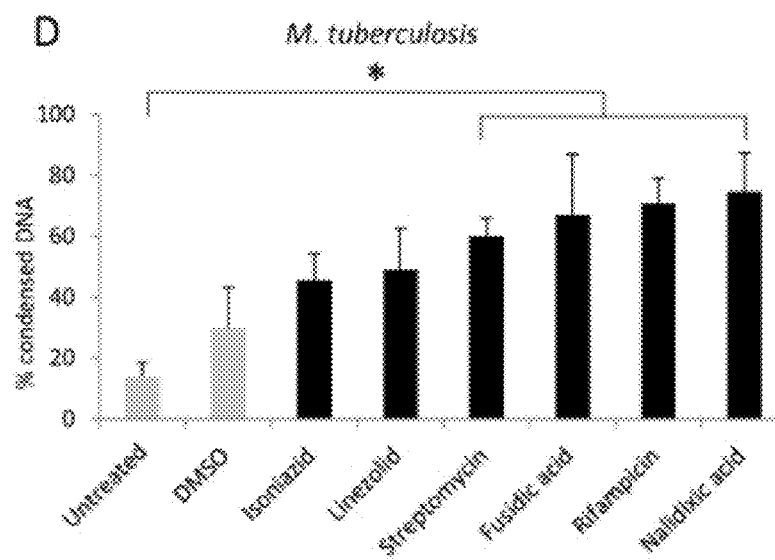
FIG. 2C                    FIG. 2D

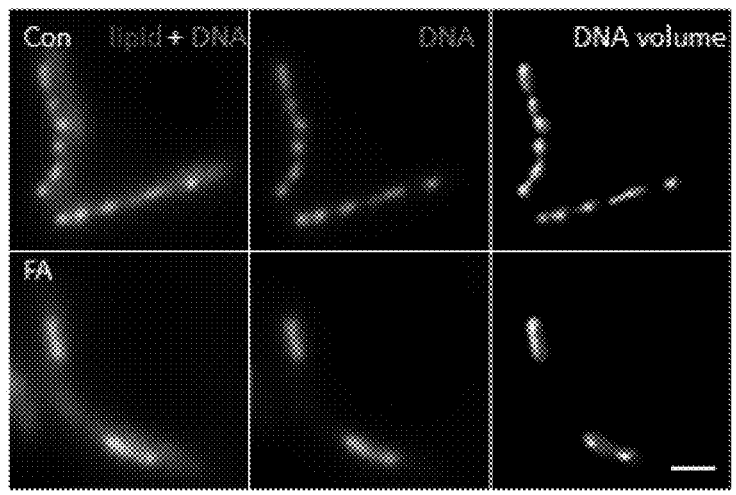 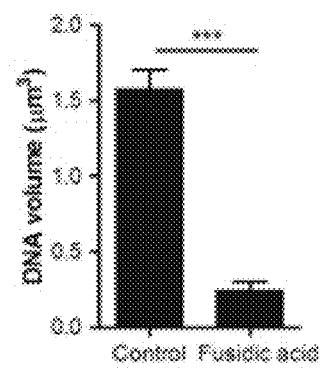
FIG. 5A  FIG. 5B
FIG. 6A
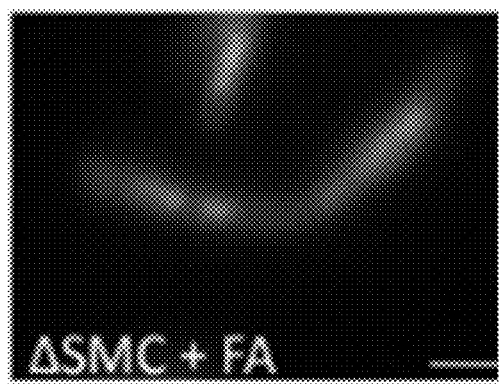
FIG. 6B

|  |  | 2hr | Day 1 | | | | Day 2 | | | Day 3 | | | Day 6 | | | |
|---|---|---|---|---|---|---|---|---|---|---|---|---|---|---|---|---|
|  |  | subset | subset | | | | subset | | | subset | | | subset | | | |
|  | n | 1 | 1 | 2 | 3 | 4 | 1 | 2 | 3 | 1 | 2 | 3 | 1 | 2 | 3 | 4 |
| FA + EIS | 9 | 5.5 |  | 6.5 | 6.5 |  | 4.8 |  |  | 3.7 |  |  | 3.7 |  |  |  |
| EIS + FA | 6 | 5.6 | 5.8 | 5.8 |  |  |  | 5.3 |  |  | 4.8 |  |  | 4.6 |  |  |
| FA + -- | 9 | 5.6 | 5.3 |  |  |  | 5.0 | 5.0 |  |  | 4.3 |  |  |  | 5.1 |  |
| EIS + -- | 9 | 5.6 |  |  |  | 7.7 |  |  | 7.0 |  |  | 7.0 |  |  |  | 7.1 |
| -- + -- | 9 | 5.6 |  |  | 7.4 | 7.4 |  |  | 7.0 |  |  | 6.9 |  |  |  | 7.1 |

FIG. 12D

COMBINATION OF A DNA CONDENSATION-INDUCING COMPOUND AND AN EIS INHIBITOR FOR ANTIBIOTIC TREATMENT

RELATED APPLICATIONS

This application claims the benefit of U.S. Provisional Application Ser. No. 62/701,373, filed Jul. 20, 2018, the entire disclosure of which is incorporated herein by this reference.

TECHNICAL FIELD

The presently-disclosed subject matter generally relates antibiotic compositions and treatment of bacterial infection. In particular, certain embodiments of the presently-disclosed subject matter relate to compositions and methods of using a combination of a DNA condensation-inducing compound and an Eis Inhibitor

BACKGROUND

Bacterial infections, including drug-resistant bacterial infections, are a significant threat world-wide. For example, tuberculosis (TB), caused by *Mycobacterium tuberculosis* infection, is the leading cause of death from an infectious disease, resulting in 10.4 million new cases world-wide, including around 500,000 humans infected by the multi-resistant form, and an estimated 1.4 million deaths in year 2015 alone. In recent years, multidrug-resistant, extensive drug-resistant, and total drug-resistant *M. tuberculosis* strains have emerged, and in some regions the percentage of patients infected by multi-drug resistant tuberculosis is well above 50%.

Treatment options for tuberculosis patients are limited, expensive, and characterized by severe side effects, especially in the case of multi-drug resistant forms. Thus, new therapeutic approaches are urgently needed. Additionally, since part of the tuberculosis casualties are caused by the reactivation of *M. tuberculosis* in granuloma of latently infected individuals, strategies for treating the latent form of this disease are essential. Uncovering novel vulnerabilities of the this and other pathogens is important to generate new therapeutic strategies.

SUMMARY

The presently-disclosed subject matter meets the above-identified needs, as will become evident to those of ordinary skill in the art after a study of information provided in this document. Advantages of the present disclosure include antifungal agents and pharmaceutical compositions including same for the treatment or prevention of a fungal condition in a subject in need thereof.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

Provided herein, in some embodiments, are methods of killing bacteria including treating the bacteria with a DNA condensation-inducing compound; and subsequently treating the bacteria with an Eis inhibitor. In one embodiment, the DNA condensation-inducing compound is an antibiotic. In another embodiment, the antibiotic is selected from the group consisting of: fusidic acid, nalidixic acid, linezolid, streptomycin, and rifampicin. In one embodiment, the Eis inhibitor is a pyrrolo[1,5-a]pyrazine-based Eis inhibitor.

In some embodiments, the bacteria is a mycobacteria. In one embodiment, the bacteria is *Mycobacterium tuberculosis*. In another embodiment, the bacteria is *Mycobacterium smegmatis*. In some embodiments, the bacteria is causing an infection in a subject. In one embodiment, the step of treating the bacteria with a DNA condensation-inducing compound includes administering the DNA condensation-inducing compound to the subject. In another embodiment, the step of subsequently treating the bacteria with the Eis inhibitor includes administering the Eis inhibitor to the subject.

Also provided herein, in some embodiments, is an antibiotic kit, comprising: a DNA condensation-inducing compound packaged together with an Eis inhibitor. In some embodiments, the DNA condensation-inducing compound is an antibiotic. In one embodiment, the antibiotic is selected from the group consisting of: fusidic acid, nalidixic acid, linezolid, streptomycin, and rifampicin. In another embodiment, wherein the Eis inhibitor is a pyrrolo[1,5-a]pyrazine-based Eis inhibitor.

In some embodiments, the kit further includes instructions for killing bacteria. In one embodiment, the bacteria is mycobacteria. In one embodiment, the bacteria is *Mycobacterium tuberculosis*. In one embodiment, the bacteria is *Mycobacterium smegmatis*. In one embodiment, the bacteria is causing an infection in a subject. In one embodiment, the instructions comprise administering the DNA condensation-inducing compound to the subject, and subsequently administering the Eis inhibitor to the subject.

Additional advantages of the present invention will become apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIGS. 1A-D show images illustrating altered localization DNA visible in *M. smegmatis* after FA treatment. (A-B) TEM-images of ultrathin (80 nm) sections of (A) untreated and (B) FA-treated *M. smegmatis* showing a single, enlarged area with typical DNA structure (*) in the FA treated bacteria. (C-D) Tomogram slices containing a semi-thick (300 nm) section of FA treated *M. smegmatis*. (C) Stacks are artificial color coded based on electron-density, with e-dense ribosome-like structures in red and DNA clusters in green. (D) Separate TEM image. Arrowhead indicates septum, * indicates typical DNA structure and all scale bars represent 500 nm.

FIGS. 2A-D show images and graphs illustrating that DNA-condensation is a generic response to antibiotic-induced stress in *Mycobacterium*. (A-B) Fluorescent microscopy images of lipid and DNA patterns in (A)*M. smegmatis* mc²155 and (B)*M. tuberculosis* mc²6030 in control and FA treatment conditions. Lipids stained with BODIPY (red), DNA stained with Hoechst 33342 (green), an overlay of the two fluorescent signals and the overlay with the bright-field image (DIC). (C) Average bacteria with condensed DNA distribution patterns in *M. smegmatis*, in control (grey bar) and after 1 hour FA-treatment (black bar, bars represents mean±standard error, n=3, $P<0.05^*$). (D)*M. tuberculosis* mc²6030 was exposed to various antibiotics to target different cellular processes. The incidence of DNA-condensation was quantified for untreated, DMSO treated as a control (grey bars) and antibiotic treated (black bars) *M. tuberculosis* mc²6030 cultures. Per condition, the percentage of bacilli with condensed DNA is displayed, which was based on three measurements of n≥20 bacteria per condition. Treatment with streptomycin, fusidic acid, rifampicin and nalidixic acid increased the percentage bacteria with condensed DNA significantly (bar represents mean±standard error, $P<0.05^*$). Scale bar represents 2 µm.

FIGS. 5A-B show an image and a graph illustrating that DNA volume decreases in response to antibiotic-induced stress. (A) Deconvolved widefield fluorescence microscopy images of lipid (Nile Red) and DNA (DAPI) patterns in (un)treated *M. smegmatis* mc2 155. Deconvolved DAPI signal was used to compute DNA volume. Scale bar represents 1 µm. (B) Quantification of DNA volume. Bars represent mean±standard deviation of 3 independent experiments (n=60 bacteria per condition). $P<0.0005^{***}$.

FIGS. 6A-B show images illustrating that DNA-condensation is independent on SMC. (A-B) DNA stained with Hoechst of Δ SMC triple mutant *M. smegmatis* mc²6 cultures (A) untreated or (B) treated with for 1 hour with Fusidic Acid (FA). Bar represents 1 µm.

FIGS. 12A-D show images and graphs illustrating that inhibition DNA acetylation after condensation DNA does not prevent DNA-condensation but improves killing *M. smegmatis*. (A) Fluorescence microscopy of DNA (green) and lipids with Nile Red stained as counterstaining (red) of *M. smegmatis* cultures treated with FA (FA), compound Eis 1a*, inhibiting the Eis enzyme (EIS) or FA and subsequently Eis inhibitor (FA→EIS), the reverse order (EIS→FA) or control (Con). (B) Similar set-up as in (A) imaged after 2 days of incubation in antibiotics. (C) Average CFU at 2 hours, 1, 2, 3 and 6 days after incubation in liquid antibiotic containing medium and plated on antibiotic free plates (average of 3 measurements of 3 independent experiments with standard error). (D) A one-way ANOVA was performed on log transformed CFU data per time point. Subsequently Student-Newman-Keuls test was applied to identify subsets of conditions with similar effects on CFU (P<0.05). Bars represent 1 µm.

DETAILED DESCRIPTION OF THE DISCLOSURE

Figure 2A:
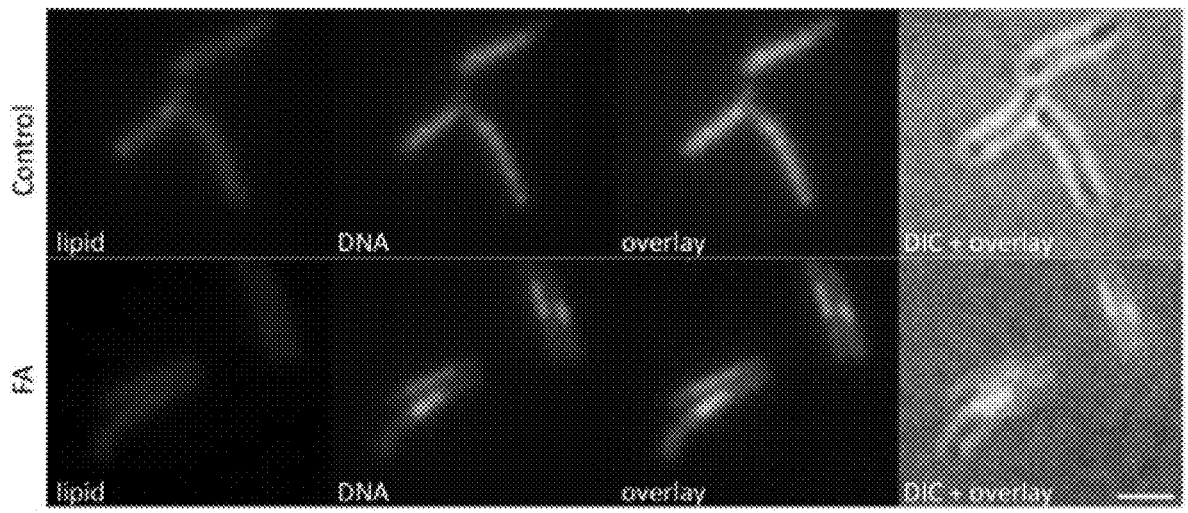

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, domesticated animal (e.g., cat, dog, etc.), livestock (e.g., cattle, horses, pigs, sheep, goats, etc.), or laboratory animals (e.g., mouse, rabbit, rat, guinea pig, fruit fly, etc.). The term does not denote a particular age or sex. Thus, adult and newborn subjects, as well as fetuses, whether male or female, are intended to be covered.

A patient refers to a subject afflicted with a disease or disorder. The term "patient" includes human and veterinary subjects. In some aspects of the disclosed methods, the subject has been diagnosed with a need for treatment of one or more disorders, such as, but not limited to, tuberculosis.

As used herein, the terms "treat," "treatment," and "treating" relate to curing or substantially curing a bacterial infection and/or ameliorating at least one symptom of the infection. These terms also refer to both therapeutic treatment and prophylactic or preventative measures, wherein the object is to prevent or slow down (lessen) an undesired pathological change or disorder, such as the development or spread of tuberculosis. For purpose of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The terms "treat," "treatment," and "treating" can also mean prolonging survival as compared to expected survival if not receiving treatment. Those in need of treatment include those already with the condition or disorder as well as those prone to have the condition or disorder or those in which the condition or disorder is to be prevented.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a specific condition.

As used herein, the phrase "identified to be in need of treatment for a disorder," or the like, refers to selection of a subject based upon need for treatment of the disorder. For example, a subject can be identified as having a need for treatment of a disorder (e.g., tuberculosis) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a preparation to a subject. Such methods are well known to those skilled in the art and include, but are not limited to, administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition.

As used herein, the term a "therapeutically effective amount" refers to an amount that is sufficient to achieve the desired therapeutic result or to have an effect on undesired symptoms, but is generally insufficient to cause adverse side effects. For example, the phrase "therapeutically effective amount" means an amount of a compound of the present disclosure that (1) treats or prevents the particular disease, condition, or disorder; (2) attenuates, ameliorates, or eliminates one or more symptoms of the particular disease, condition, or disorder; or (3) prevents or delays the onset of one or more symptoms of the particular disease, condition, or disorder described herein.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The presently-disclosed subject matter includes antibiotic compositions and methods for treatment of bacterial infection. In some embodiments, the presently-disclosed subject matter includes a method of killing bacteria, which involves treating the bacteria with a DNA condensation-inducing compound. In some embodiments, treating the bacteria with a DNA condensation-inducing compound includes administering an effective amount of the compound or compounds to a subject in need thereof. As will be recognized by the skilled artisan, compounds that induce DNA condensation are known in the art. Suitable DNA condensation-inducing compounds include, but are not limited to, antibiotics, such as fusidic acid, nalidixic acid, linezolid, streptomycin, and/or rifampicin. Upon review of the present application, the skilled artisan will recognize that the DNA condensation-inducing compound can be selected in view of the context in which the method is being practiced. In one example, the selection of the compound may differ if the method is being practiced in connection with an animal subject or not. In another example, the selection of the compound may differ if the method is being practiced in connection with an animal subject under different administration protocols, e.g., topical administration, oral administration, administration by injection, etc.

In some embodiments, such as in the clinically relevant *M. tuberculosis*, DNA-condensation is a physiological response to antibiotic stress or starvation conditions. Under normal conditions, this response is reversible, as DNA returns to the initial decondensed state after withdrawal of the stress-inducing agent. However, the instant inventors have discovered that blocking this decondensation step by inhibition of histone-like protein acetylation sensitizes bacteria to the stress-inducing agent and dramatically reduces their survival. This sensitization to the stress-inducing agent represents a previously unknown vulnerability of *M. tuberculosis*.

Accordingly, in some embodiments, after treating the bacteria with a DNA condensation-inducing compound, the method includes subsequently treating the bacteria with an Eis inhibitor. In some embodiments, treating the bacteria with an Eis inhibitor includes administering an effective amount of the Eis inhibitor to a subject in need thereof. In some embodiments, the Eis Inhibitor is a pyrrolo[1,5-a]pyrazine-based Eis inhibitor. In some embodiments, the Eis inhibitor is an Eis inhibitor as set forth in U.S. patent application Ser. Nos. 15/381,901 and 15/836,666.

In some embodiments of the method, the bacteria is causing an infection in a subject. In this regard, the method can be used as an antibiotic treatment for the subject. Accordingly, in some embodiments, the method may include a step of identifying a subject with a bacterial infection. For example, in some embodiments, the infection is caused by a mycobacteria and the method disclosed herein may be used to target mycobacteria. In one embodiment, the infection is caused by *Mycobacterium tuberculosis* and the method may be used to target *Mycobacterium tuberculosis*. In another embodiment, the infection is caused by *Mycobacterium smegmatis* and the method can be used to target *Mycobacterium smegmatis.*

The presently-disclosed subject matter also includes an antibiotic kit that includes a DNA condensation-inducing compound packaged together with an Eis Inhibitor. The included DNA condensation-inducing compound and Eis inhibitor are as described above. In some embodiments, the kit can further include a device useful for administration of the compounds.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This Example describes the discovery of a vulnerability of *Mycobacterium tuberculosis* using high resolution microscopy techniques. It was demonstrated that the DNA of *M. tuberculosis* can condense under stressful conditions such as starvation and antibiotic treatment. The DNA condensation is reversible and specific for viable bacteria. The mechanism by which mycobacteria recover from the condensed state involves DNA binding histone-like proteins and can be blocked by inhibiting posttranslational modifications of the histone-like proteins, but possibly also other proteins, via acetylation using inhibitors like Eis 1a*. Blocking the recovery from the condensed state weakens the bacteria.

More specifically, this Example focuses on the preservation of bacterial genome integrity by the temporary condensation of chromosomal DNA, a process demonstrated to occur during latency and other stressful conditions in *Escherichia coli, Bacillus subtilis, Helicobacter pylori, cyanobacteria*, and *Deinococcus radiodurans*. This phenomenon was observed for the first time during electron microscopic imaging of starved *E. coli*, and led to the hypothesis that a compact structure of DNA and DNA-binding proteins might act as a physical barrier. Stress-induced DNA-condensation was also shown to promote homology-driven repair of DNA double strand breaks in *E. coli*, further demonstrating a role for nucleoid-condensation in maintaining genome integrity during stress. Moreover, DNA-condensation is thought to be associated with quiescence, and quiescent mycobacteria are able to condense their DNA. Interestingly, quiescent *Mycobacterium smegmatis* with condensed nucleoids display reduced metabolism and increased tolerance to stress and antibiotics.

The mechanisms driving nucleoid-condensation remain to be identified. Computational simulations of idealized DNA structural monomers showed that attraction is sufficient to collapse a chain of large structural DNA monomers and that entropic forces exerted by molecular crowding can cause compaction of chromosomes. These computational modeling studies combined with physical manipulation demonstrated that *E. coli* chromosome behaves as a loaded entropic spring in vivo. Besides the entropic forces, this process also involves nucleoid associated proteins. These nucleoid associated proteins (NAPs) are homologous to histones and especially well studied in *E. coli*. Here, NAPs interact with DNA and influence replication, transcription and compaction. As mycobacterial NAPs have limited homology to *E. coli* NAPs, a number of mycobacterial DNA binding proteins have been identified as NAPs only recently. HupB was described to be binding to the origin of replication in *M. smegmatis*. Deletion of Rel was shown to affect the lipid and DNA distribution in *M. smegmatis*. Also in *M. smegmatis*, overexpression of histone like protein H-NS or Rv3852 from *M. tuberculosis*, results in a less compact nucleoid morphology. In addition, the change in the acetylation state of the nucleoid associated proteins can cause a shift in the DNA localization in this microorganism.

As described herein, after inducing DNA condensation, and subsequent blocking of acetylation of DNA binding proteins, the DNA localization in the bacteria is altered. Importantly under these conditions, *Mycobacterium smegmatis* did not replicate and its survival was significantly reduced. These results demonstrate that agents that block recovery from the condensed state of the nucleoid can be exploited as antibiotic. The combination of fusidic acid and inhibition of acetylation of DNA binding proteins, via the Eis enzyme, potentiate the efficacy of fusidic acid by 10 and the Eis inhibitor to 1000 fold. Hence, successive treatment with antibiotics and drugs interfering with recovery from DNA-condensation constitutes a novel approach for treatment of tuberculosis and related bacterial infections.

Fusidic Acid (FA), and several other antibiotics (fusidic acid (250 μg/ml; Sigma-Aldrich), nalidixic acid (330 μg/ml; Sigma-Aldrich), isoniazid (2 μg/ml; Sigma-Aldrich), linezolid (20 μg/ml; Sigma-Aldrich), streptomycin (20 μg/ml; SERVA), rifampicin (20 μg/ml; Sigma-Aldrich), can induce condensation of the DNA. Furthermore, an Eis inhibitor, can reduce survival of mycobacteria by successively exposing bacteria to the Eis inhibitor when mycobacteria display stress-induced DNA-condensation. Examples of Eis inhibitors are set forth in U.S. patent application Ser. Nos. 15/381,901 and 15/836,666, which are incorporated herein by this reference.

Such Eis inhibitors can suppress the aminoglycoside acetylation activity of Eis in vitro and in *M. tuberculosis*/*M. smegmatis* cultures. The pyrrolo[1,5-a]pyrazine-based Eis inhibitor 1a* was shown to inhibit kanamycin acetylation biochemically, biologically, and structurally already (ref), and was examined as a potentiator of the effects of antibiotic treatment. No direct effect of Eis 1a* on DNA condensation was observed in *M. smegmatis* mc2155. In addition, the growth of *M. smegmatis* liquid cultures was not inhibited by Eis 1a*. However, when given in combination with EIS and FA, viability staining indicates that the majority of bacteria with unorganized DNA are dead. Also, a drop in OD was observed in FA-Eis 1a* treated cultures on day 2, 3, and 6 and the number of CFUs was significantly reduced in these cultures compared to FA treated and Eis 1a*-FA treated *M. smegmatis*. These results indicate that interfering with acetylation of the DNA-binding protein MtHU after antibiotic treatment results in higher killing efficiency.

MATERIALS AND METHODS

Bacterial Strains and Culturing Conditions

*M. smegmatis* mc$^2$155, *M. smegmatis* mc$^2$6, *M. smegmatis* mc$^2$3449 mc$^2$3449 structural maintenance of chromosomes (SMC) triple deletion mutant and *M. tuberculosis* mc$^2$6030 were grown in Middlebrook 7H9 medium supplemented with 0.05% Tween-80, 0.2% glycerol, and 10% Oleic Albumin Dextrose Catalase (OADC) at 37° C. while shaking to an OD$_{600}$ ranging between 0.1 and 0.6 at the start of the experiment. Pantothenate-auxotroph strain mc$^2$6030 was supplemented with 24 µg/ml pantothenate. For starvation experiments, cultures were grown in PBS/Tween-80 at 37° C. while shaking.

Antibiotic Solutions

Bacteria were subjected to 20 times the MIC50 of fusidic acid (250 µg/ml; Sigma-Aldrich), nalidixic acid (330 µg/ml; Sigma-Aldrich), isoniazid (2 µg/ml; Sigma-Aldrich), linezolid (20 µg/ml; Sigma-Aldrich), streptomycin (20 µg/ml; SERVA), rifampicin (20 µg/ml; Sigma-Aldrich), Eis inhibitor 1a* (10 µM), or DMSO (solvent control; Merck Millipore) for 1 hour.

Transmission Electron Microscopy and Tomography

*M. smegmatis* mc$^2$155 or *M. tuberculosis* mc$^2$6030 was subjected to FA for 1 hour, fixed with McDowell fixative in 0.1 M sodium cacodylate buffer and postfixed with kaliumhexacyanoferrate (VWR) and 1% osmiumtetroxide (Electron Microscopy Sciences) in cacodylate buffer. Samples were embedded in gelatin and after ethanol dehydration, embedded in Epon (Ladd Research). Grids covered with formvar were used to collect 50-80 nm sections made using a Leica EM FC6 (Leica). Sections were stained using uranyl acetate and lead citrate. Electron microscopy images were collected using a FEI Tecnai™ transmission electron microscope with a LaB$_6$ filament (Denka) at 120 kV. For tomography, 100/200 nm thick sections of epon embedded *M. smegmatis* with or without FA were imaged with ±60° tilt series, with 5° increments. Images were aligned using Fourier filtered cross correlation and reconstructed by SIRT (Simultaneous Iterative Reconstruction Technique) with 25 iterations using the Inspect3D Xpress software.

Fluorescence Microscopy and Combined Light and Electron Microscopy

For fluorescence microscopy on fixed samples, cultures were fixed by resuspension in fixative with paraformaldehyde and glutaraldehyde (Sigma-Aldrich) for 4 hours. Next, fixed bacteria were transferred to storage buffer with paraformaldehyde. DNA was visualized by Hoechst 33342 (Thermofischer). Cell membranes and lipid inclusions were visualized by either BODIPY® 558/568 C$_{12}$ (4,4-difluoro-5-(2-thienyl)-4-bora-3a,4a-diaza-s-indacene-3-dodecanoic acid; Molecular Probes) or Nile Red (9-diethylamino-5H-benzo[a]phenoxazine-5-one; Sigma-Aldrich) for 5 minutes in the dark at room temperature. After incubation, coverslips were mounted by using VectaShield Mounting Medium (Vector Industries). Wide-field fluorescence microscopy images were collected using a Leica DM-RA light microscope equipped with a 100× Plan Apo 1.4 Phaco3 oil-immersion objective lens. Confocal fluorescence microscopy images were collected using a Leica SP8-X SMD confocal fluorescence microscope fitted with a 63× Plan Apo NA 1.4 CS3 oil-immersion objective lens (Leica). Excitation of fluorophores was done using a 100 mW White Light Laser (Leica) and detected using a variable bandpass filter (Leica) with HyD or photomultiplier tube detectors (Leica). For CLEM, fixed *M. smegmatis* mc$^2$155 cultures were stained for DNA and lipids and incubated on Carbon coated golden reference finder grids (Electron Microscopy Sciences). Grids were subsequently analyzed with confocal fluorescence microscopy and Transmission Electron Microscopy, and the images were matched using Photoshop.

Monitoring Mycobacterial Survival

*M. smegmatis* mc$^2$155 overnight cultures were treated with FA, EIS inhibitor 1a*, or a combination hereof. Cultures were treated with antibiotic for 1 hour before second antibiotic was administered. Before treatment, and after 2 hours and at day 1,2,3 and 6, the OD$_{600}$ was determined with a spectrophotometer, and a sample of the culture was fixed, or plated in a dilution series on 7H10 plates in triplo. At day 2, the antibiotic treatment was repeated. At least 3 independent experiments were quantified per condition.

Live Cell Imaging

For live cell imaging, bacteria were stained with the LIVE/DEAD® BacLight™ Bacterial Viability Kit. *M. smegmatis* mc$^2$155 or *M. tuberculosis* mc$^2$6030 suspension was incubated on PolyL-Lysine-coated multiwell microscopy slides in the dark at room temperature. FA was added before coverslips were mounted, and bacteria were monitored using wide-field fluorescence microscopy. *M. smegmatis* cultures were treated with FA and time-lapse images (time interval of 2 or 5 minutes) were acquired using a fully motorized Leica DMi8 inverted widefield fluorescence microscope (Leica Microsystems, Wetzlar, Germany) equipped with culture incubator. Images were recorded with a high numerical aperture 63× oil immersion objective (HC PL APO CS2 63.0×1.40 OIL UV; Leica Microsystems) [immersion oil, Leica Type N, n$_D$(refractive index)=1.518 (at 23° C.); Leica Microsystems, Wetzlar, Germany] using a 16-bit Hamamatsu ORCA—Flash4.0 V2 sCMOS C11440-

22CU camera (Hamamatsu Photonics, Hamamatsu, Japan) with Leica Application Suite X image acquisition software and a GFP filter (Ex: 450-490 nm, Dc: 495 nm, Em: 500-550 nm; Leica Microsystems, Wetzlar, Germany). After deconvolution from ~4-5 z-sections with 0.5 µm spacing, images were analyzed by local background subtraction and thresholding using Huygens Software (Scientific Volume Imaging, SVI, Hilversum, The Netherlands). Final image adjustments were done using ImageJ 1.49 s (National Institutes of Health, Bethesda, Md.).

DNA Volume Quantification

Z-stack Wide-field FM images of fixed *M. smegmatis* mc$^2$155 stained for DNA and lipids were collected at 200 nm increments. Deconvolution and DNA volume quantification was subsequently performed using standard deconvolution parameters of Huygens Professional software (Scientific Volume Imaging, SVI, Hilversum, The Netherlands). Average volume was determined for 60 bacteria per condition per experiment and standard deviation was calculated with 2-tailed T-test.

Statistical Analysis CFUs

In all experiments, factor correction was applied to remove systematic differences between the different measuring sessions needed to obtain the results. In case of 2 experimental conditions, Student's t-test was applied. More than 2 conditions were compared with 1-way Analysis Of Variance (ANOVA), when more conditions were compared at different time points, a 2-way ANOVA always showed a significant interaction between culture conditions and time points, indicating that the effects of the culture conditions dependent on the time of analysis. To further dissect these effects, a 1-way ANOVA per time point was performed. After each 1-way ANOVA a post-hoc Student-Newman-Keuls was applied to determine subsets of conditions with similar effects; conditions in different subsets differ significantly from each other P-values <0.05 were considered significant.

RESULTS

Stress-Induced Ultrastructural Rearrangement of DNA in *M. smegmatis* and *M. tuberculosis*

Previous studies using transmission electron microscopy (TEM) have identified striated bundles of crystalline DNA in different bacterial species. To determine if mycobacteria undergo similar ultrastructural changes, TEM was performed on ultrathin sections of early log phase *M. smegmatis* mc$^2$155 control cultures (OD<0,8) and cultures treated with the antibiotic fusidic acid (FA). FA inhibits protein synthesis by blocking GTPase activity of ribosomal elongation factor G. In FA treated *M. smegmatis*, bundles of DNA were localized in a single compact nucleoid, whereas DNA in untreated bacilli was more dispersed in multiple smaller nucleoids (FIGS. 1A-B). To enhance the resolution of smaller ultra-structures such as DNA and ribosomes, tomographic analysis was performed on semi-thick sections of Epon-embedded *M. smegmatis*. Using differences in (electron) density, enlarged, striated clusters of DNA (in green) which did not overlap with ribosomes (in red, FIGS. 1C-D and FIGS. 8A-B) were identified.

Figure 8A:
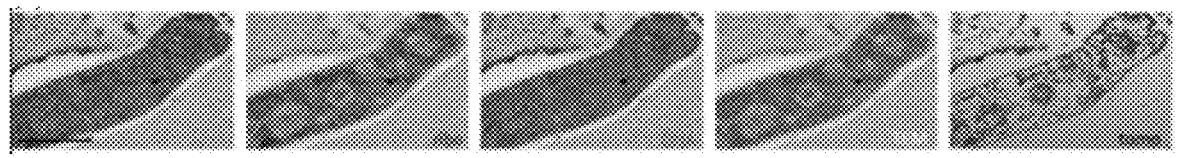
FIGS. 8A-E show images illustrating DNA-condensation imaged with EM and CLEM. (A-B) Tomogram slices containing a semi-thick (300 nm) section of (A) *M. smegmatis* control or (B) FA treated. Stacks are artificial color coded based on electron-density, with in red e-dense ribosome-like structures, in green DNA clusters, top section (TEM) and the segmentations of the tomograms separate from the TEM image (tomo). Scale bars represent 500 nm and A' or B' movie focusing through the section, depicting different layers. (C) Combined Light and Electron Microscopy images of a small group of intact, PFGA fixed *M. smegmatis* treated with FA for 1 hour and stained with BODIPY (red, lipid), DAPI-Hoechst (green, DNA arrowheads indicate clustered DNA), the combination of DNA and Lipid and combinations of EM and DNA and Lipid, bar represents 2 µm. (D) High magnification CLEM. (E) EM image of fixed *M. smegmatis* from (C) demonstrating e-lucent areas in the bacteria that correspond to the DNA clusters (arrowheads). Bar represents 2 µm.
Figure 8B:
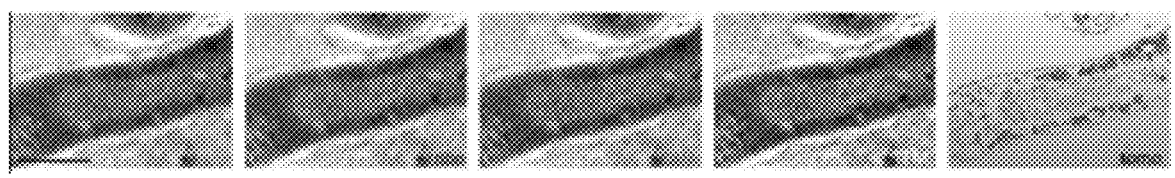
Figure 8C:
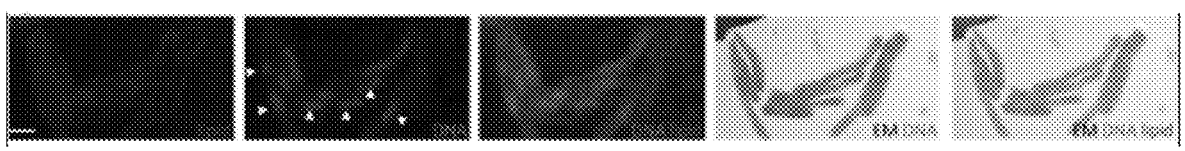
Figure 8D:
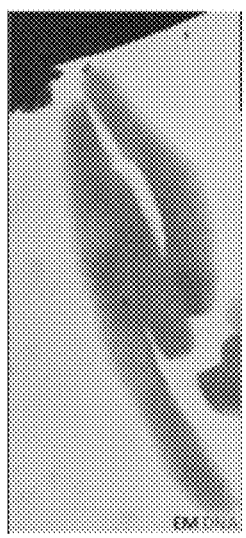
Figure 8E:
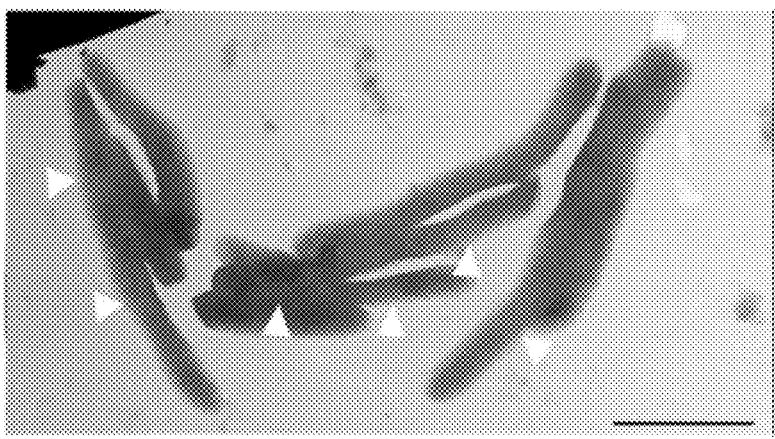
Figure 9A:
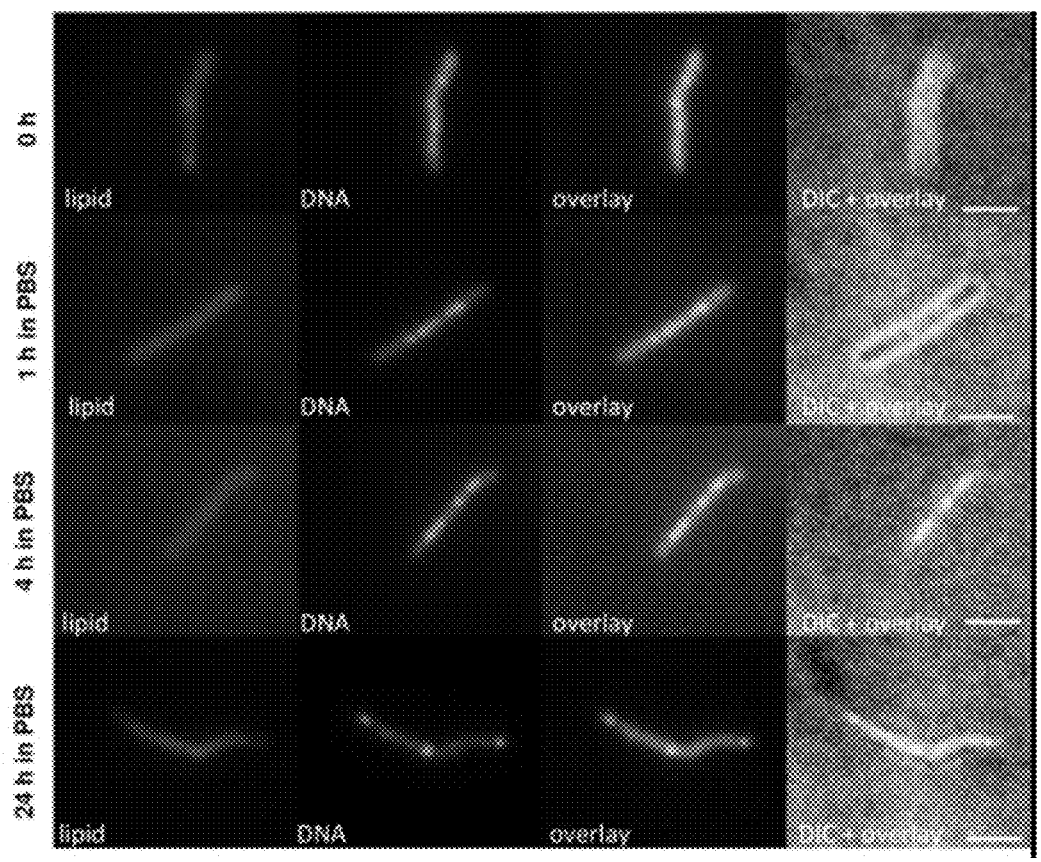
FIGS. 9A-B show images and a graph illustrating that *M. smegmatis* condenses DNA during starvation. (A) *M. smegmatis* was cultured in ADC-supplemented Middlebrook 7H9 medium before being transferred to PBS. Bacteria were starved in this medium for 0, 1, 4 and 24 hours. Lipid distribution (Nile Red) and DNA localization (Hoechst in green) and overlay with DIC detected at the different time points. (B) Genome localization was quantified and categorized in dispersed, condensed and polar at 0, 1, 4, 24 hours. Bars represent mean±standard error n=2, based on >500 bacteria. Scale bars represent 2 µm.
Figure 9B:
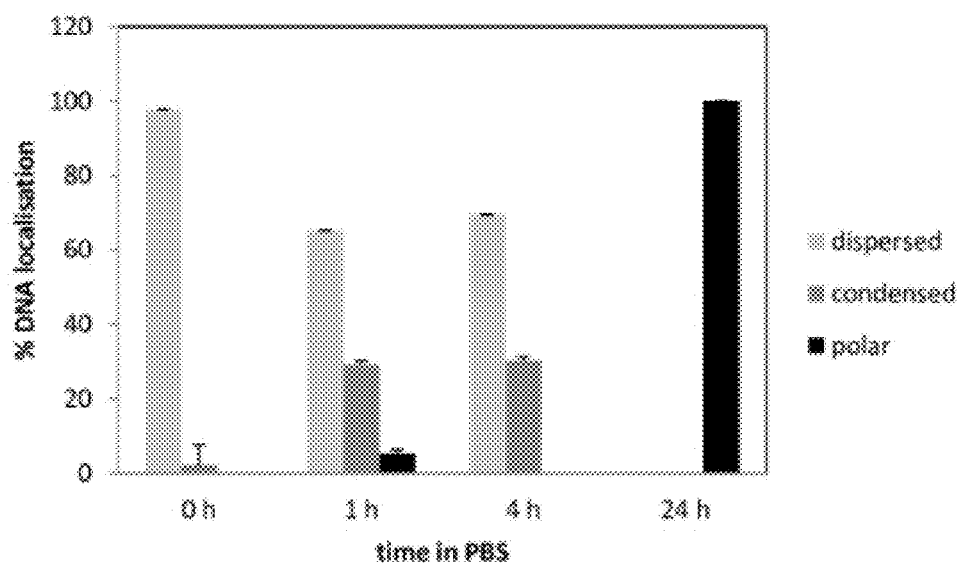

To confirm that the induced rearrangements indeed involve DNA, Correlative Light and Electron Microscopy (CLEM) was performed. To this end, intact *M. smegmatis* were fixed and applied to finder grids to enable tracing individual bacteria first using fluorescence microscopy (FM) and subsequently with EM. CLEM analysis demonstrated that the electron-lucent, ribosome-free clusters co-localized with the fluorescence signal of DNA in the bacteria (FIGS. 8C-E). Taken together, these data indicate that nucleoid condensation in distinct areas takes place in *M. smegmatis* upon FA treatment.

DNA-condensation is a General Stress Response in Mycobacteria

Figure 2B:
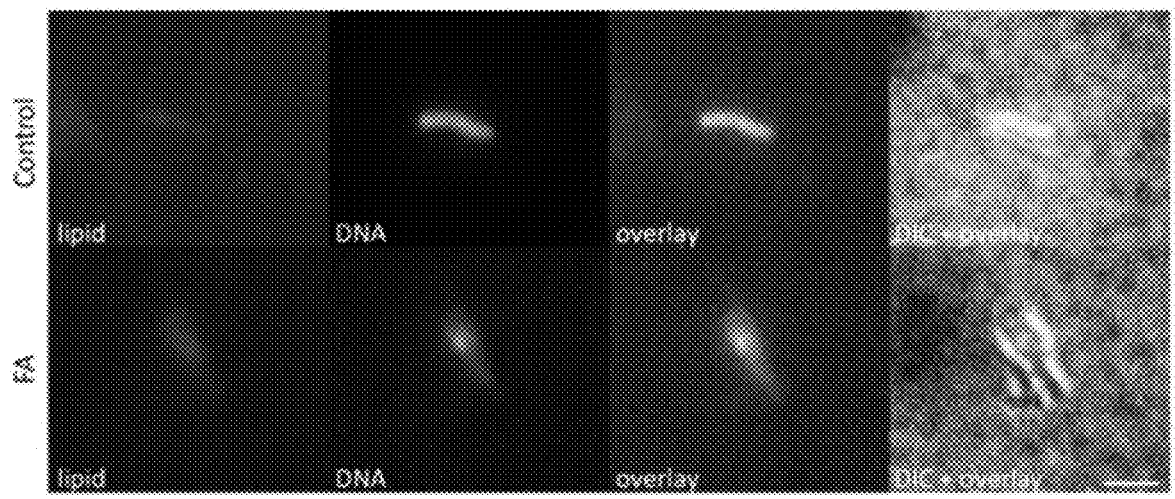
Figure 3A:
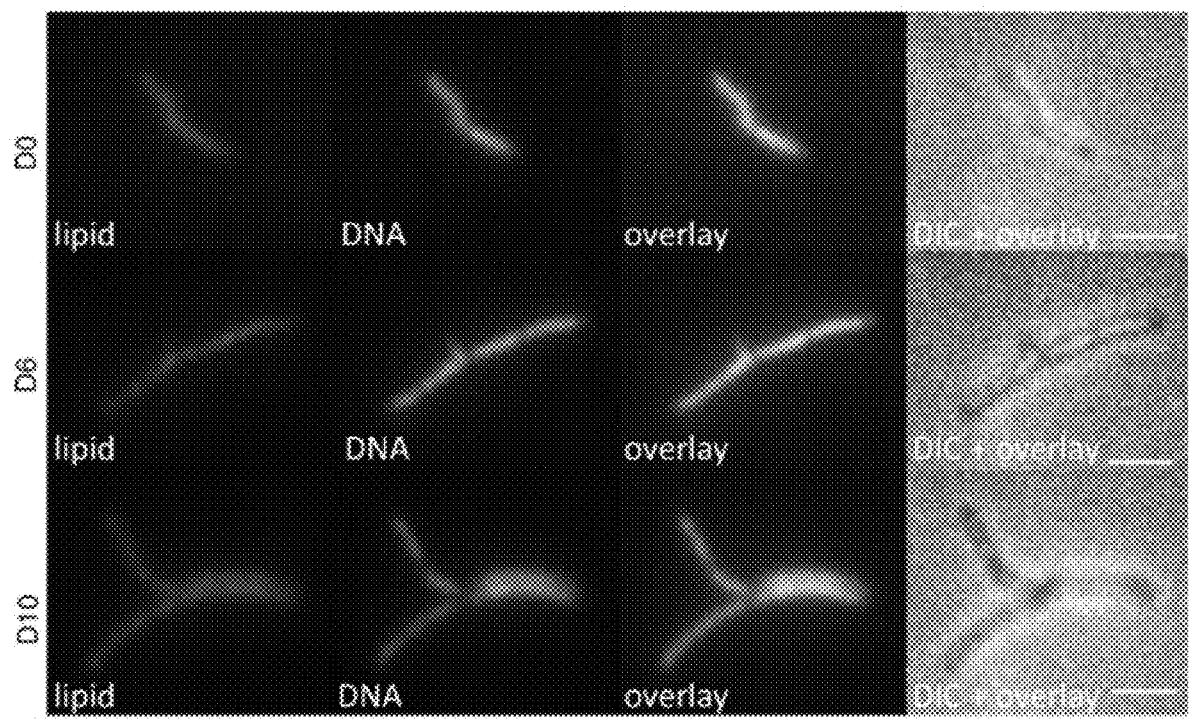
FIGS. 3A-B show images and a graph illustrating that *M. tuberculosis* condenses DNA during starvation. *M. tuberculosis* mc²6030 was cultured in ADC-supplemented Middlebrook 7H9 medium before being starved in PBS. (A) Lipid distribution and DNA localization was imaged using Nile Red (red) and Hoechst (green) respectively at day 0,6 and 10. (B) Percentage bacteria with condensed DNA was quantified at day 0,3,6 and 10. Values represent mean percentage bacteria with condense DNA±standard error, pooled data of 2 measurements, $P<0.05^*$. Scale bars represent 2 µm.
Figure 3B:
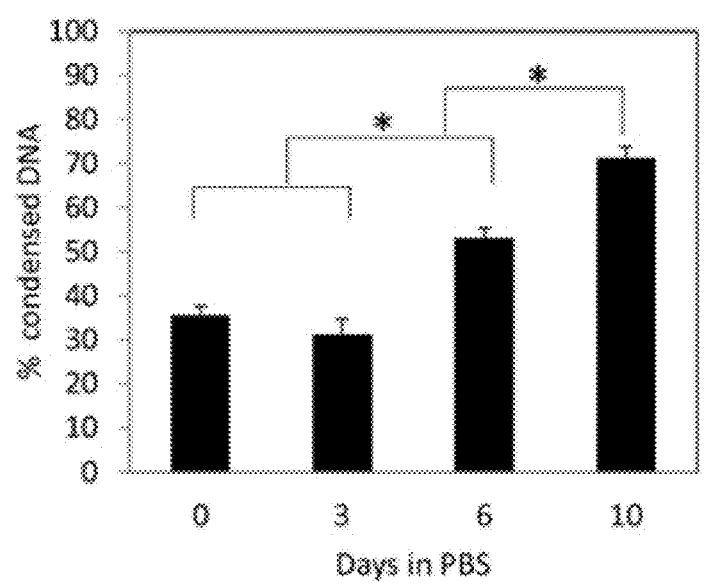

To gain further insights into the prevalence of nucleoid aggregation upon stress, *M. smegmatis* mc$^2$155 and *M. tuberculosis* mc$^2$6030 were treated with antibiotics or mock-treated, and localization of DNA was categorized and quantified by FM. During early log phase, DNA of untreated *M. smegmatis* appeared distributed across the cell in a distinctive pattern, forming a chain of small nucleoids. However, more than 90% of the bacteria condensed their DNA into a single nucleoid after FA treatment (FIG. 2A). Similarly, *M. tuberculosis* mc$^2$6030 subjected to the same experimental conditions condensed their DNA into a single nucleoid (FIG. 2B). For *M. smegmatis* mc$^2$155 cultures treated with FA or mock-treated, DNA localization was categorized and quantified after 1 hour of antibiotic stress, more than 80% of the bacteria condensed their nucleoid (FIG. 2C). Thus, within 1 hour of antibiotic-induced stress, the DNA in mycobacteria rearranges and condenses into a single clump.

To evaluate whether DNA-condensation in mycobacteria is a generic response to antibiotic-induced stress, *M. tuberculosis* mc$^2$6030 was exposed to a variety of antibiotics that hamper DNA replication, transcription, translation, and cell wall synthesis (FIG. 2D). Treatment with streptomycin, fusidic acid, rifampicin, and nalidixic acid resulted in a significantly increased fraction of bacilli with condensed DNA, indicating that DNA-condensation is a generic response to antibiotic-induced stress in *M. tuberculosis*.

To evaluate if DNA-condensation might occur under conditions of stress caused by agents other than antibiotics, nutrient starvation was carried out by culturing *M. tuberculosis* and *M. smegmatis* in phosphate-buffered saline (PBS) after regular culturing. These culturing conditions need to be maintained for 14 days or longer to induce quiescence in *M. tuberculosis*, and several hours to starve *M. smegmatis*. At different time points, the incidence of DNA-condensation was evaluated (FIGS. 3A-B and FIGS. 9A-B). Nucleoid condensation was apparent in *M. smegmatis* after 1-4 hours of culturing in PBS. For *M. tuberculosis*, a slow growing bacterium which is extremely resistant to starvation, a gradual increase in DNA-condensation was visible after 10-14 days. Interestingly, the nucleoid was relocated to the poles of *M. smegmatis* after 24 hours, whereas this condensation pattern was evident neither for *M. tuberculosis*, nor for *M. smegmatis* treated with FA. In summary, these experiments demonstrate DNA-condensation in response to starvation- and antibiotic-induced stress, demonstrating that DNA-condensation is a generic response to stress in mycobacteria.

DNA-condensation Responses are Limited to Viable Mycobacteria

Figure 10A:
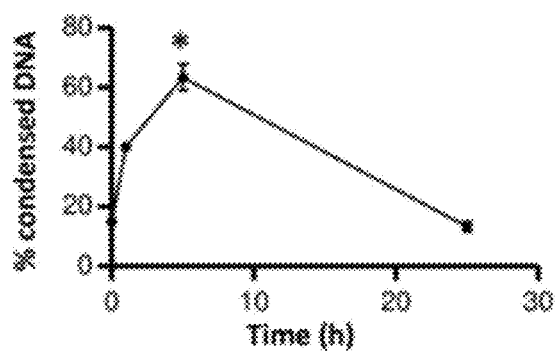
FIGS. 10A-C show a graph and images illustrating that *M. tuberculosis* condensation is reversible. The reversibility of DNA-condensation after antibiotic treatment was evaluated. (A) At time points pre- and post-treatment of *M. tuberculosis* mc²6030 with FA for 1 hour, the incidence of DNA-condensation was quantified in fixed samples stained with DAPI using confocal fluorescence microscopy. Values represent mean±standard error based on 8 measurements of n≥20 bacteria per time point, originating from 2 independent experiments $P<0.05^*$. (B) DNA in response to antibiotic-induced stress, schematically illustrated, with green resembling DNA-localization. (C) Live cell imaging combined with bacterial viability staining applied to live *M. smegmatis* 5 min after FA treatment and imaged at t=0 till 28 minutes with 5 minutes intervals.
Figure 10B:
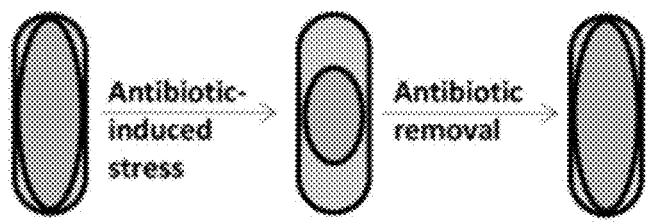
Figure 10C:
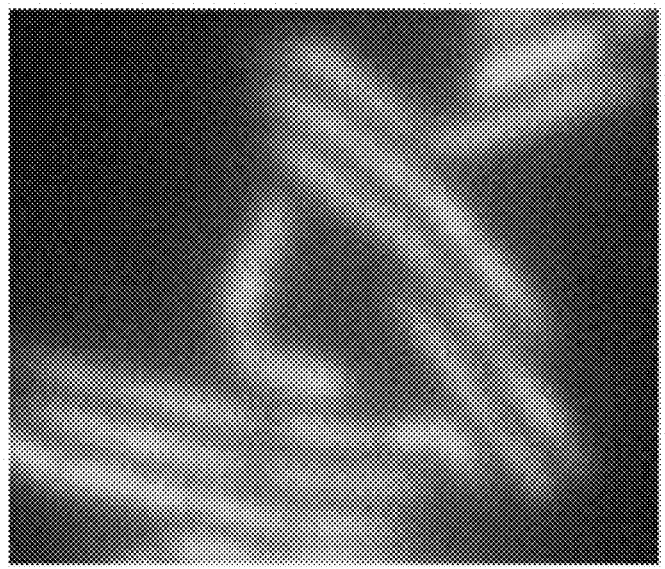
Figure 11A:
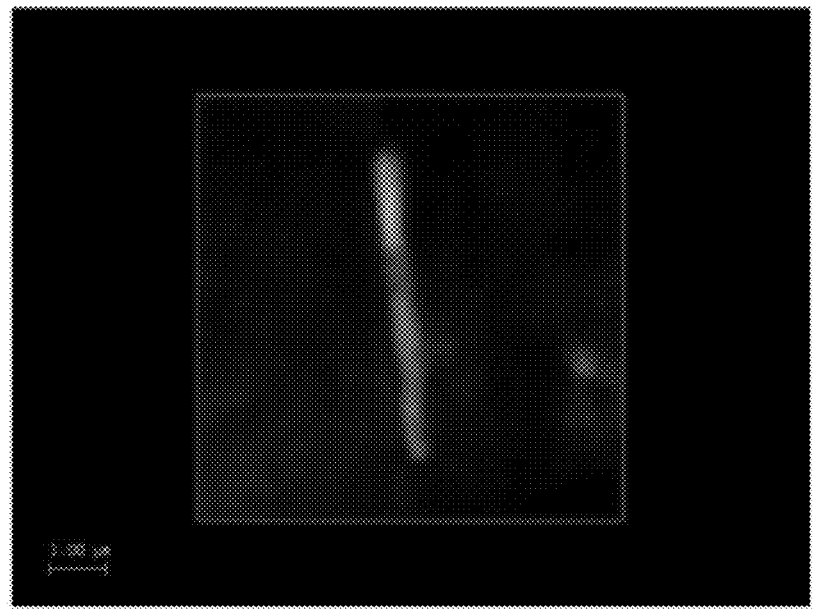
FIGS. 11A-B show images illustrating live cell imaging of FA treated *M. smegmatis*. (A-B) Two *M. smegmatis* bacteria are imaged 5 min after FA treatment, stained with bacterial viability staining and imaged at (A) t=0 till 38 min with 2 min intervals and (B) with stills.
Figure 11B:
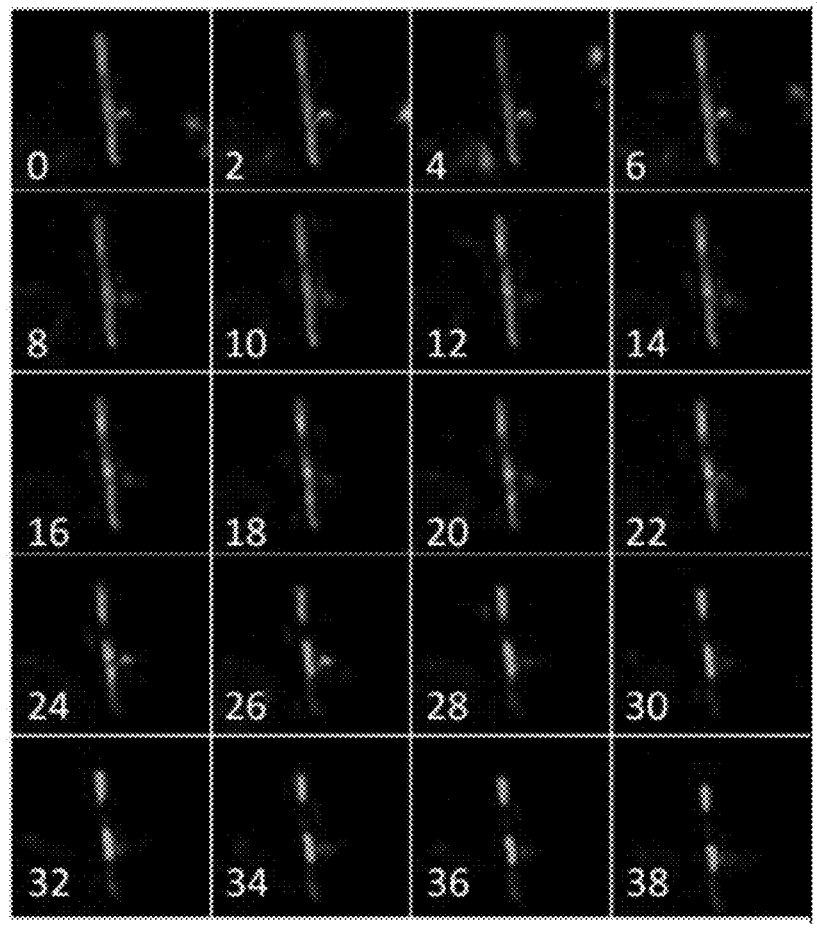
Figure 12A:
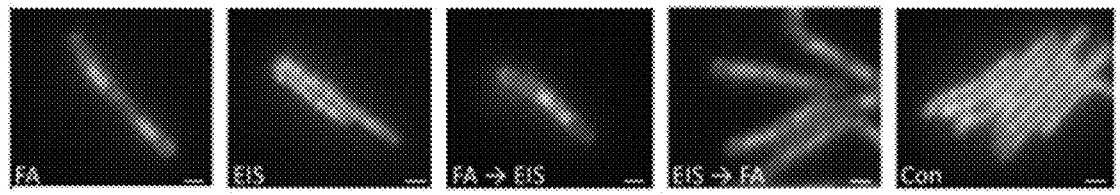
Figure 12B:
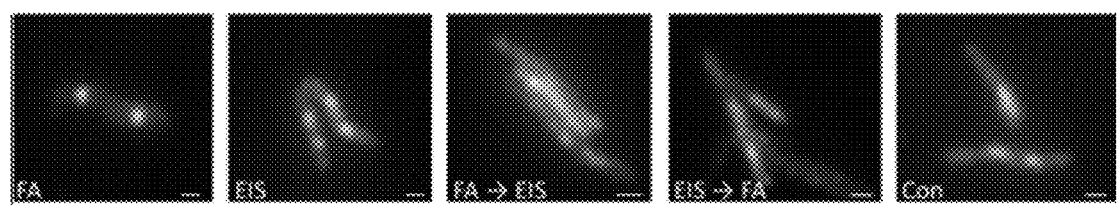
Figure 12C:
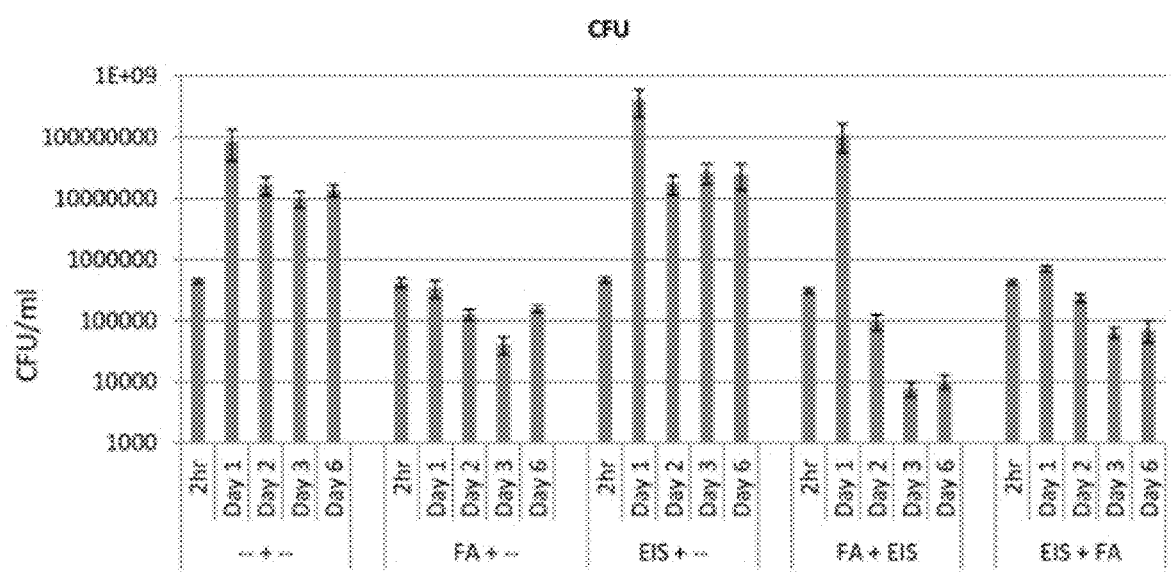

Condensation of DNA could be an indication of cell death, similar to eukaryotic apoptosis and it has indeed been reported that that nucleoid-condensation accompanies cell death in *E. coli*, whereas others have reported that DNA-condensation upon stress is reversible, suggesting that it is restricted to viable bacteria. To determine whether DNA-condensation is reversible in mycobacteria, *M. tuberculosis* mc$^2$6030 cultures were treated with FA for 1 hour and washed to remove the antibiotic, followed by regular culturing for 24 hours (FIGS. 10A-C). The incidence of DNA-condensation increased until 6 hours after treatment, followed by a gradual reduction. This decrease could not be attributed to the progression of cell division because the duplication time of *M. tuberculosis* is ~20 hours. Thus, DNA-condensation is a reversible process in mycobacteria.

Figure 4A:
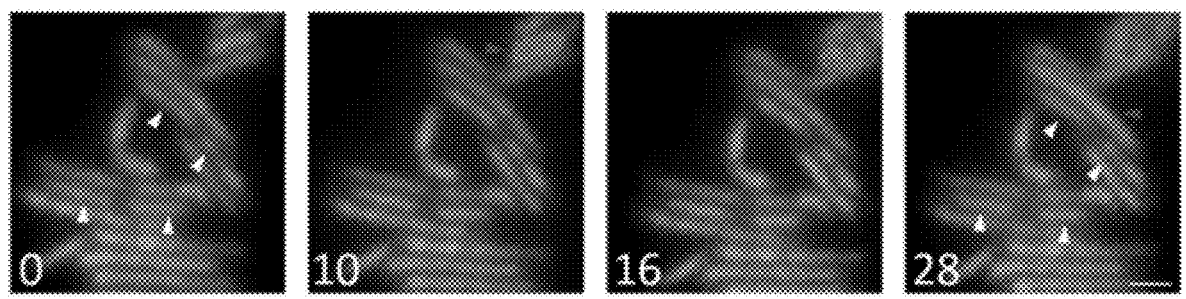
FIGS. 4A-C show images and graphs illustrating that Mycobacteria with condensed DNA are viable. (A) To evaluate the viability of treated *M. smegmatis* with condensed DNA at single cell resolution, a bacterial viability staining was applied to live bacteria 5 minutes after FA treatment and imaged at t=0, 10, 16 and 28 minutes. Live bacteria (green) condense their DNA (white arrowheads), and in red, dying bacteria with dispersed DNA (red arrowheads). Scale bar represents 1 µm. (B-C) DNA distribution of (B) nonviable and (C) viable *M. tuberculosis* mc²6030 bacteria were quantified as dispersed (normal) and condensed. Grey bars represent quantification of *M. tuberculosis* mc²6030 control and black bars represent quantification after 1 h treatment with FA. Bacteria stained with Syto9- and PI-fluorescence were fixed with PFA and images were generated by confocal fluorescence microscopy. Bars represent mean±standard error. Data were pooled from 3 measurement sessions and occurrence of DNA condensation in viable control and FA-treated cells was compared with a Chi2-test, $P<0.05^*$.
Figure 4B:
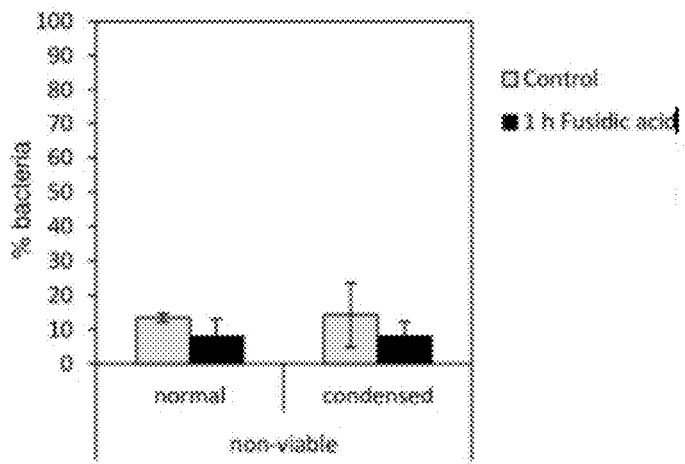
Figure 4C:
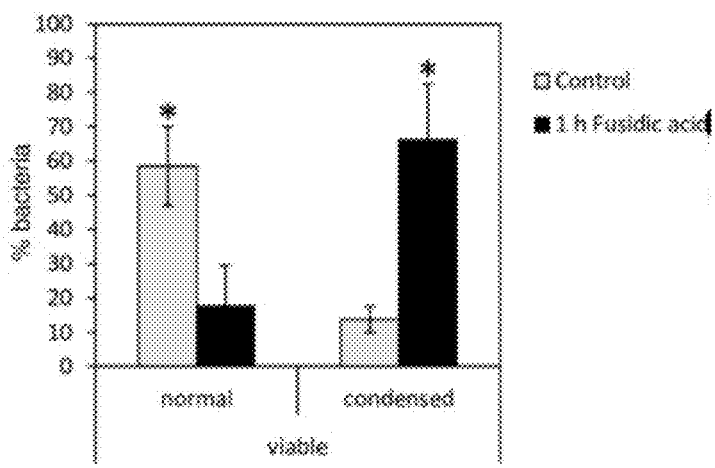
Figure 7A:
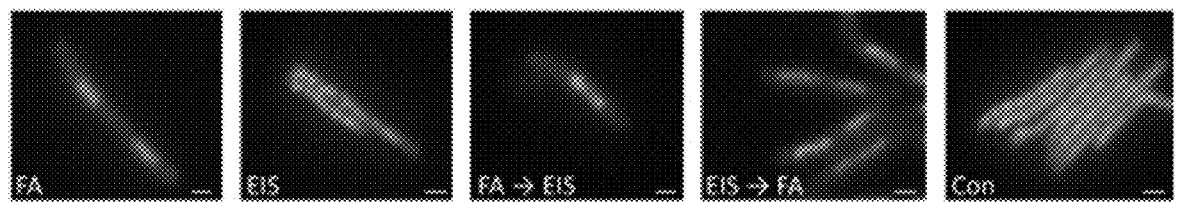
FIGS. 7A-D show images and a graph illustrating that inhibition DNA acetylation after condensation DNA improves killing *M. smegmatis*. (A) Fluorescence micros-copy of DNA of *M. smegmatis* treated with FA, compound Eis 1a*, inhibiting the Eis enzyme (EIS) or FA and subsequently Eis inhibitor (FA→EIS), the reverse order (EIS→FA) or control (Con) (Nile Red stained as counterstaining is presented in FIG. 12A). (B) Similar set-up as in (A) imaged after 2 days of incubation (Nile Red stained as counterstaining is presented in FIG. 12B). (C) Relative Colony Forming Units (CFU) based on untreated controls at 6 days after incubation in liquid antibiotic containing medium and plated on antibiotic free plates (relative CFU is calculated based on untreated controls and average of 3 independent experiments with standard error and * for significant differences to control $P<0.05$). (D) Representative colonies from 10 µl 7H9 medium at a dilution of $10^2$, $10^4$ or $10^5$ with FA, Eis inhibitor or antibiotic combinations or control after incubation for 6 days in 7H9 and subsequently grown on 7H10 plate without antibiotics. Bars represent 1 µm.
Figure 7B:
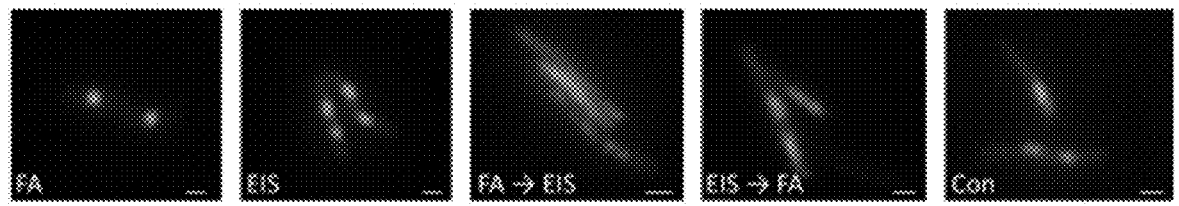
Figure 7C:
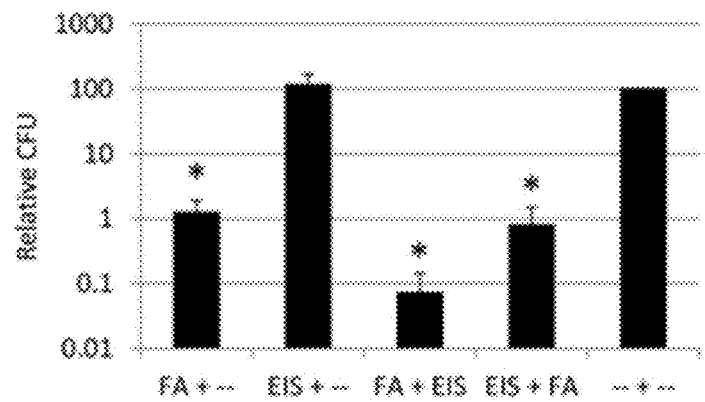
Figure 7D:
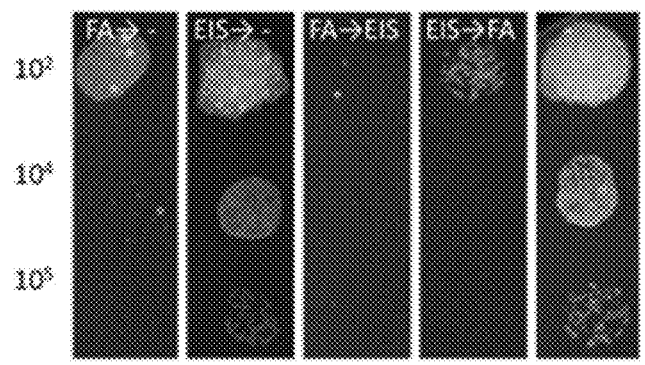

To support these findings, the viability of mycobacteria with condensed nucleoids was evaluated after FA treatment at single-cell resolution using a viability staining, which allows distinguishing between viable and inviable bacteria based on the integrity of the cell wall. Live-cell imaging of *M. smegmatis* was started 5 minutes after FA addition, when the nucleoid is uncondensed. Differences in nucleoid localization became visible after 10 minutes, and the first bacteria converted from viable (green) to inviable (red) after 16 minutes (FIGS. 4A and 10A-11B). However, while bacteria that condensed their DNA survived the entire duration of the experiment (white arrowheads in FIG. 4A), the dying bacteria did not condense their nucleoid (red arrowheads). To support this observation, the incidence of DNA-condensation was evaluated in FA-treated and control *M. tuberculosis* mc$^2$6030 cultures that were fixed after the viability staining (FIGS. 4B-C). 1 hour after FA treatment, the percentage of viable bacteria with condensed DNA increased significantly, whereas the percentage of nonviable bacteria with condensed DNA did not differ between the untreated and FA-treated cultures.

In summary, DNA-condensation upon antibiotic-induced stress is a reversible process, limited to viable mycobacteria, and therefore, it might be part of the survival strategy of *M. tuberculosis* under stress conditions, rather than a manifestation of cell death.

Altered DNA Distribution is DNA Condensation

To determine whether the observed DNA redistribution is a result of condensation or rearrangement, the average 3D volume of the DNA clusters was measured in *M. smegmatis* cultures incubated with or without FA for 1 hour (FIG. 5A). A significantly larger average cluster volume was observed in the control versus the FA treated bacteria (1.58 and 0.24 µm$^3$, respectively FIG. 5B), confirming DNA condensation under the latter experimental condition.

SMCs Are Not Involved in DNA-condensation Upon Stress

As the aforementioned experiments suggested that DNA-condensation might be a survival strategy, it was speculated that interference with this process would sensitize bacteria to antibiotic treatments. Both DNA-condensation and de-condensation are likely to be essential for the recovery from stress and progress of cell division. DNA-binding proteins are probable participants in this process, and several DNA-binding proteins involved in regulating the DNA condensation state have already been identified. In addition to the nucleoid associated proteins described above, the structural maintenance of chromosomes (SMC) proteins are highly conserved factors involved in chromosome organization and compaction in eukaryotes and most bacteria.

There are three SMC paralogs in *M. smegmatis*. MSMEG_2423 is conserved in all mycobacterial species and shares homology with the SMC from gram positive bacteria. EptC and MSMEG_0370 are MukB like proteins and expression of EptC interferes with the segregation of plasmids with pAL5000 origin of replication by manipulating plasmid DNA topology. To investigate whether these SMCs play a role in FA dependent nucleoid condensation, the triple SMC deletion knock out mc$^2$3449 was compared to it's isogenic strain mc$^2$155 before and after FA treatment. Surprisingly, the DNA in the triple deletion knock out mc$^2$3449 still condensed into nucleoids, similar to the control strain. More importantly, DNA condensation was clearly visible after FA treatment, suggesting that these SMCs are redundant for this phenotype (FIGS. 6A-B).

Blocking Acetylation after DNA Condensation Kills Mycobacteria

Ideally, DNA condensation or de-condensation could be manipulated by inhibitors specific to bacteria and neutral to humans. As bacteria and eukaryotes have distinct histone-like proteins, these proteins could represent a selective antibiotic-target. Multiple different histone-like proteins affect the organization of the bacterial genome. For instance, Rv3852 is a histone-like protein involved in several pleiotropic phenotypic changes, including DNA compaction, as *M. smegmatis* overexpressing Rv3852 show a dispersed genome localization. Recently, it was demonstrated that acetylation of a histone-like protein termed MtHU by the enzyme Eis reduces its DNA-binding capacity, leading to decompaction of DNA. Thus, the DNA-binding properties of mycobacterial histone-like proteins are at least partly regulated by posttranslational modifications such as acetylation. Therefore, it was next investigated whether interfering with acetylation affects the condensation state of the DNA.

Several highly potent and selective Eis inhibitors have been developed, suppressing the aminoglycoside acetylation activity of Eis in vitro and in *M. tuberculosis* and *M. smegmatis* cultures. The pyrrolo[1,5-a]pyrazine-based Eis inhibitor 1a* was shown to inhibit kanamycin acetylation biochemically, biologically and structurally, and therefore it was examined whether this inhibitor could block DNA-condensation. At MIC$_{50}$, Eis 1a* treated *M. smegmatis* mc$^2$155 cultures did not reveal DNA-condensation (FIGS. 7A and 12A-D). In addition, at 2 hours of incubation, Eis 1a* did not affect FA-induced DNA-relocalisation, irrespective of whether it was added before (EIS→FA) or after FA (FA→EIS), indicating that inhibiting EIS does not influence the FA induced DNA-condensation.

As the bactericidal effect of EIS inhibition might take a few days to develop, effects of the combination treatment might be likewise delayed. Therefore, DNA localisation was monitored for several days. Untreated and Eis 1a* treated bacilli grown for 2 days (FIGS. 7B and 12A-D) displayed condensed DNA similar to that observed under starvation conditions in PBS (FIGS. 9A-B), which can be attributed to the high OD of these cultures. However, bacilli treated first with FA for 1 hour and subsequently by Eis 1a* for 1 hour (FA→EIS) showed an amorphous DNA distribution at this time point, whereas bacteria treated in the reverse order (EIS→FA), or by FA alone, still displayed condensed DNA. These results suggest that acetylation is involved in recovery of the structural organisation of the nucleoid. The amorphous DNA distribution could have an effect on the survival of mycobacteria, and thus growth of cultures treated with FA, Eis 1a*, or the successively administered combinations was monitored by determining CFU on antibiotic free 7H10 plates.

Colony forming ability of cultures treated with FA→Eis 1a* on day 2, 3, and 6 was significantly reduced (FIGS. 12A-D), as compared to those treated with FA alone and with Eis 1a*→FA (FIGS. 7C-D and 12A-D (P<0.05)). Thus, interfering with acetylation of DNA-binding proteins such as MtHU after antibiotic treatment results in increased cytotoxicity and the order of administration of the successive FA→Eis 1a* treatment is important. The amorphous DNA distribution detected in bacteria cultured under these conditions indeed correlates with reduced survival. In summary, these results suggest that the EIS inhibitor can interfere with the recovery after DNA condensation which renders mycobacteria more vulnerable to antibiotic treatments.

DISCUSSION

DNA-condensation is thought to preserve genome integrity in bacteria and in mycobacteria condensed DNA is detected as foci in dividing bacteria, in log versus stationary—phase, after starvation in PBS for *M. tuberculosis* (FIGS. 3A-B) and for *M. smegmatis*, and after treatment with different antibiotics (FIGS. 2A-D). Condensation of DNA thus appears to be a generic response to various stress conditions and this Example extendS this conclusion to *M. tuberculosis* and *M. smegmatis*, which condense their DNA in response to stress.

Recently, cryo-electron tomography demonstrated that viral phage-infected bacteria assemble the membrane-wrapped nucleus-like structures, which are different from the membrane-less DNA condensates described here. The authors demonstrated that the compact DNA is dynamic and allows for viral DNA replication. These results show that DNA condensation in mycobacteria is dynamic, reversible and unlikely to be associated with cell death, as suggested by others. Furthermore, the detected involvement of acetylation in the DNA (de)condensation process may resemble mammalian regulation of chromatin compaction that is partly driven by histone acetylation. Interestingly, even though conclusive data are not available, it has been suggested that the condensed heterochromatin in mammalian cells is more resistant to double stranded breakage induction, as compared to euchromatin, and associated with increased radioresistance. DNA compaction may thus represent a widely preserved response to stress, which could be of benefit in the early evolutionary history of life when harsh environmental conditions may have continuously threatened genomic integrity.

The mechanism driving DNA condensation is not yet understood, but the live-cell imaging experiments demonstrate that it is a relatively fast process, as condensation occurred within 10 minutes after stress-induction. Others have suggested that condensation may be a product of entropic forces, molecular crowding and actions of NAPs or other DNA binding proteins and its fast nature observed here is in agreement with at least the first two of these suggestions. However, the instant results demonstrate that the participation of SMCs is unlikely (FIGS. 6A-B) like the acetylation of DNA binding proteins. On the other hand, NAPs could be involved in recovery after condensation as overexpression of DNA binding proteins resulted in decompaction of DNA and the recovery after condensation can be inhibited by blocking acetylation in general, and presumably more specifically of DNA binding histone-like proteins.

New strategies for drug administration are urgently needed, especially to treat the quiescent and multidrug-resistant *M. tuberculosis* strains. The ongoing clinical trials mostly focus on identifying high-efficacy treatment regimens based on combining new (bedaquiline and delamanid) and old antibiotics. Accordingly, the current WHO recommendation for treatment of multi-drug resistant tuberculosis in some patients with limited options includes a combination therapy or concomitant use of multiple drugs. The results disclosed herein suggest a more refined, conceptually novel strategy where a stress-inducing (antibiotic) agent is first used to provoke a protective response in the pathogen and subsequently the cytotoxic effect is potentiated by inhibiting the recovery from this protective response. Accordingly, the order of administration of these drugs is crucial for the treatment outcome. Indeed, it was found that while exposing bacteria to the acetylation inhibitor Eis 1a* after FA-induced DNA condensation dramatically enhanced the cytotoxicity, the same combination failed to achieve similar effects when the inhibitor was administered before DNA condensation. Thus far, a comparable approach has not been considered and the only drug that binds and condenses bacterial chromosomes to kill both Gram-negative and Gram-positive species is the antimicrobial polyhexamethylene biguanide (PHMB).

The cytotoxicity analysis presented here focused on the activity of EIS 1a* inhibitor in *M. smegmatis* which in combination potentiated the efficacy of fusidic acid by 10 fold. For the application as an effective antimicrobial strategy the decrease in CFU should be higher and clearly effective in *M. tuberculosis*. While preliminary experiments showed that structurally unrelated sulphonamide acetylation inhibitor is not active in *M. tuberculosis* (data not shown), it is believed that EIS 1a* and a library of its derivatives are active in *M. tuberculosis*. In addition, and without wishing to be bound by theory, it is believed that *M. tuberculosis*-optimized inhibitors have immediate impact on rational design of combination treatment strategies exploiting protective DNA condensation as a new Achilles' heel of mycobacteria.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

WHO, Global tuberculosis report 2017, WHO publications on tuberculosis World Health Organization, Geneva, Switzerland, 2017.

M. Zignol, A. S. Dean, N. Alikhanova, S. Andres, A. M. Cabibbe, D. M. Cirillo, A. Dadu, A. Dreyer, M. Driesen, C. Gilpin, R. Hasan, Z. Hasan, S. Hoffner, A. Husain, A. Hussain, N. Ismail, M. Kamal, M. Mansjo, L. Mvusi, S. Niemann, S. V. Omar, E. Qadeer, L. Rigouts, S. Ruesch-Gerdes, M. Schito, M. Seyfaddinova, A. Skrahina, S. Tahseen, W. A. Wells, Y. D. Mukadi, M. Kimerling, K. Floyd, K. Weyer, and M. C. Raviglione, Population-based resistance of *Mycobacterium tuberculosis* isolates to pyrazinamide and fluoroquinolones: results from a multicountry surveillance project. The Lancet. Infectious diseases 16 (2016) 1185-92.

C. Dye, and B. G. Williams, The population dynamics and control of tuberculosis. Science 328 (2010) 856-61.

S. G. Wolf, D. Frenkiel, T. Arad, S. E. Finkel, R. Kolter, and A. Minsky, DNA protection by stress-induced biocrystallization. Nature 400 (1999) 83-5.

B. T. Smith, A. D. Grossman, and G. C. Walker, Localization of UvrA and effect of DNA damage on the chromosome of *Bacillus subtilis*. Journal of bacteriology 184 (2002) 488-93.

P. Ceci, L. Mangiarotti, C. Rivetti, and E. Chiancone, The neutrophil-activating Dps protein of *Helicobacter pylori*, HP-NAP, adopts a mechanism different from *Escherichia coli* Dps to bind and condense DNA. Nucleic acids research 35 (2007) 2247-56.

K. Murata, S. Hagiwara, Y. Kimori, and Y. Kaneko, Ultrastructure of compacted DNA in cyanobacteria by high-voltage cryo-electron tomography. Scientific reports 6 (2016) 34934.

M. Eltsov, and J. Dubochet, Fine structure of the *Deinococcus radiodurans* nucleoid revealed by cryoelectron microscopy of vitreous sections. Journal of bacteriology 187 (2005) 8047-54.

Y. Qu, C. J. Lim, Y. R. Whang, J. Liu, and J. Yan, Mechanism of DNA organization by *Mycobacterium tuberculosis* protein Lsr2. Nucleic acids research 41 (2013) 5263-72.

N. Shechter, L. Zaltzman, A. Weiner, V. Brumfeld, E. Shimoni, Y. Fridmann-Sirkis, and A. Minsky, Stress-induced condensation of bacterial genomes results in re-pairing of sister chromosomes: implications for double strand DNA break repair. The Journal of biological chemistry 288 (2013) 25659-67.

E. S. Rittershaus, S. H. Baek, and C. M. Sassetti, The normalcy of dormancy: common themes in microbial quiescence. Cell host & microbe 13 (2013) 643-51.

M. L. Wu, C. L. Chan, and T. Dick, Rel Is Required for Morphogenesis of Resting Cells in *Mycobacterium smegmatis*. Frontiers in microbiology 7 (2016) 1390.

M. L. Wu, M. Gengenbacher, J. C. Chung, S. L. Chen, H. J. Mollenkopf, S. H. Kaufmann, and T. Dick, Developmental transcriptome of resting cell formation in *Mycobacterium smegmatis*. BMC genomics 17 (2016) 837.

M. L. Wu, M. Gengenbacher, and T. Dick, Mild Nutrient Starvation Triggers the Development of a Small-Cell Survival Morphotype in Mycobacteria. Frontiers in microbiology 7 (2016) 947.

T. N. Shendruk, M. Bertrand, H. W. de Haan, J. L. Harden, and G. W. Slater, Simulating the entropic collapse of coarse-grained chromosomes. Biophys J 108 (2015) 810-20.

J. Pelletier, K. Halvorsen, B. Y. Ha, R. Paparcone, S. J. Sandler, C. L. Woldringh, W. P. Wong, and S. Jun, Physical manipulation of the *Escherichia coli* chromosome reveals its soft nature. Proceedings of the National Academy of Sciences of the United States of America 109 (2012) E2649-56.

S. C. Dillon, and C. J. Dorman, Bacterial nucleoid-associated proteins, nucleoid structure and gene expression. Nat Rev Microbiol 8 (2010) 185-95.

J. Holowka, D. Trojanowski, K. Ginda, B. Wojtas, B. Gielniewski, D. Jakimowicz, and J. Zakrzewska-Czerwinska, HupB Is a Bacterial Nucleoid-Associated Protein with an Indispensable Eukaryotic-Like Tail. MBio 8 (2017).

S. Ghosh, S. S. Indi, and V. Nagaraja, Regulation of lipid biosynthesis, sliding motility, and biofilm formation by a membrane-anchored nucleoid-associated protein of *Mycobacterium tuberculosis*. Journal of bacteriology 195 (2013) 1769-78.

S. Ghosh, B. Padmanabhan, C. Anand, and V. Nagaraja, Lysine acetylation of the *Mycobacterium tuberculosis* HU protein modulates its DNA binding and genome organization. Molecular microbiology 100 (2016) 577-88.

J. M. Ruijter, H. H. Thygesen, O. J. Schoneveld, A. T. Das, B. Berkhout, and W. H. Lamers, Factor correction as a tool to eliminate between-session variation in replicate experiments: application to molecular biology and retrovirology. Retrovirology 3 (2006) 2.

S. Levin-Zaidman, D. Frenkiel-Krispin, E. Shimoni, I. Sabanay, S. G. Wolf, and A. Minsky, Ordered intracellular RecA-DNA assemblies: a potential site of in vivo RecA-mediated activities. Proceedings of the National Academy of Sciences of the United States of America 97 (2000) 6791-6.

M. Gengenbacher, S. P. Rao, K. Pethe, and T. Dick, Nutrient-starved, non-replicating *Mycobacterium tuberculosis* requires respiration, ATP synthase and isocitrate lyase for maintenance of ATP homeostasis and viability. Microbiology 156 (2010) 81-7.

D. J. Dwyer, D. M. Camacho, M. A. Kohanski, J. M. Callura, and J. J. Collins, Antibiotic-induced bacterial cell death exhibits physiological and biochemical hallmarks of apoptosis. Molecular cell 46 (2012) 561-72.

H. A. Eskandarian, P. D. Odermatt, J. X. Y. Ven, M. T. M. Hannebelle, A. P. Nievergelt, N. Dhar, J. D. McKinney, and G. E. Fantner, Division site selection linked to inherited cell surface wave troughs in mycobacteria. Nat Microbiol 2 (2017) 17094.

N. L. Sullivan, K. A. Marquis, and D. Z. Rudner, Recruitment of SMC by ParB-parS organizes the origin region and promotes efficient chromosome segregation. Cell 137 (2009) 697-707.

M. W. Panas, P. Jain, H. Yang, S. Mitra, D. Biswas, A. R. Wattam, N. L. Letvin, and W. R. Jacobs, Jr., Noncanonical SMC protein in *Mycobacterium smegmatis* restricts maintenance of *Mycobacterium* fortuitum plasmids. Proceedings of the National Academy of Sciences of the United States of America 111 (2014) 13264-71.

A. Garzan, M. J. Willby, K. D. Green, O. V. Tsodikov, J. E. Posey, and S. Garneau-Tsodikova, Discovery and Optimization of Two Eis Inhibitor Families as Kanamycin Adjuvants against Drug-Resistant *M. tuberculosis*. ACS medicinal chemistry letters 7 (2016) 1219-1221.

A. Garzan, M. J. Willby, K. D. Green, C. S. Gajadeera, C. Hou, O. V. Tsodikov, J. E. Posey, and S. Garneau-Tsodikova, Sulfonamide-Based Inhibitors of Aminoglycoside Acetyltransferase Eis Abolish Resistance to Kanamycin in *Mycobacterium tuberculosis*. Journal of medicinal chemistry 59 (2016) 10619-10628.

A. Garzan, M. J. Willby, H. X. Ngo, C. S. Gajadeera, K. D. Green, S. Y. Holbrook, C. Hou, J. E. Posey, O. V. Tsodikov, and S. Garneau-Tsodikova, Combating Enhanced Intracellular Survival (Eis)-Mediated Kanamycin Resistance of *Mycobacterium tuberculosis* by Novel Pyrrolo[1,5-a]pyrazine-Based Eis Inhibitors. ACS infectious diseases (2017).

M. J. Willby, K. D. Green, C. S. Gajadeera, C. Hou, O. V. Tsodikov, J. E. Posey, and S. Garneau-Tsodikova, Potent Inhibitors of Acetyltransferase Eis Overcome Kanamycin Resistance in *Mycobacterium tuberculosis*. ACS chemical biology 11 (2016) 1639-46.

W. Chen, K. D. Green, O. V. Tsodikov, and S. Garneau-Tsodikova, Aminoglycoside multiacetylating activity of the enhanced intracellular survival protein from *Mycobacterium smegmatis* and its inhibition. Biochemistry 51 (2012) 4959-67.

K. D. Green, T. Biswas, A. H. Pang, M. J. Willby, M. S. Reed, O. Stuchlik, J. Pohl, J. E. Posey, O. V. Tsodikov, and S. Garneau-Tsodikova, Acetylation by Eis and Deacetylation by Rv1151c of *Mycobacterium tuberculosis* HupB: Biochemical and Structural Insight. Biochemistry 57 (2018) 781-790.

M. Almiron, A. J. Link, D. Furlong, and R. Kolter, A novel DNA-binding protein with regulatory and protective roles in starved *Escherichia coli*. Genes & development 6 (1992) 2646-54.

A. Martinez, and R. Kolter, Protection of DNA during oxidative stress by the nonspecific DNA-binding protein Dps. Journal of bacteriology 179 (1997) 5188-94.

A. Badrinarayanan, T. B. Le, and M. T. Laub, Bacterial chromosome organization and segregation. Annual review of cell and developmental biology 31 (2015) 171-99.

G. S. Gordon, and A. Wright, DNA segregation in bacteria. Annual review of microbiology 54 (2000) 681-708.

I. Santi, N. Dhar, D. Bousbaine, Y. Wakamoto, and J. D. McKinney, Single-cell dynamics of the chromosome replication and cell division cycles in mycobacteria. Nature communications 4 (2013) 2470.

J. Vaubourgeix, G. Lin, N. Dhar, N. Chenouard, X. Jiang, H. Botella, T. Lupoli, O. Mariani, G. Yang, O. Ouerfelli, M. Unser, D. Schnappinger, J. McKinney, and C. Nathan, Stressed mycobacteria use the chaperone ClpB to sequester irreversibly oxidized proteins asymmetrically within and between cells. Cell host & microbe 17 (2015) 178-90.

V. Chaikeeratisak, K. Nguyen, K. Khanna, A. F. Brilot, M. L. Erb, J. K. Coker, A. Vavilina, G. L. Newton, R. Buschauer, K. Pogliano, E. Villa, D. A. Agard, and J. Pogliano, Assembly of a nucleus-like structure during viral replication in bacteria. Science 355 (2017) 194-197.

T. Kouzarides, Chromatin modifications and their function. Cell 128 (2007) 693-705.

K. Storch, I. Eke, K. Borgmann, M. Krause, C. Richter, K. Becker, E. Schrock, and N. Cordes, Three-dimensional cell growth confers radioresistance by chromatin density modification. Cancer Res 70 (2010) 3925-34.

M. Falk, E. Lukasova, and S. Kozubek, Higher-order chromatin structure in DSB induction, repair and misrepair. Mutat Res 704 (2010) 88-100.

R. de Vries, DNA condensation in bacteria: Interplay between macromolecular crowding and nucleoid proteins. Biochimie 92 (2010) 1715-21.

A. H. Diacon, A. Pym, M. Grobusch, R. Patientia, R. Rustomjee, L. Page-Shipp, C. Pistorius, R. Krause, M. Bogoshi, G. Churchyard, A. Venter, J. Allen, J. C. Palomino, T. De Marez, R. P. van Heeswijk, N. Lounis, P. Meyvisch, J. Verbeeck, W. Parys, K. de Beule, K. Andries, and D. F. Mc Neeley, The diarylquinoline TMC207 for multidrug-resistant tuberculosis. The New England journal of medicine 360 (2009) 2397-405.

M. T. Gler, V. Skripconoka, E. Sanchez-Garavito, H. Xiao, J. L. Cabrera-Rivero, D. E. Vargas-Vasquez, M. Gao, M. Awad, S. K. Park, T. S. Shim, G. Y. Suh, M. Danilovits, H. Ogata, A. Kurve, J. Chang, K. Suzuki, T. Tupasi, W. J. Koh, B. Seaworth, L. J. Geiter, and C. D. Wells, Delamanid for multidrug-resistant pulmonary tuberculosis. The New England journal of medicine 366 (2012) 2151-60.

A. Matteelli, R. Centis, L. D'Ambrosio, G. Sotgiu, M. Tadolini, E. Pontali, A. Spanevello, and G. B. Migliori, WHO strategies for the programmatic management of drug-resistant tuberculosis. Expert review of respiratory medicine 10 (2016) 991-1002.

K. Chindera, M. Mahato, A. K. Sharma, H. Horsley, K. Kloc-Muniak, N. F. Kamaruzzaman, S. Kumar, A. McFarlane, J. Stach, T. Bentin, and L. Good, The antimicrobial polymer PHMB enters cells and selectively condenses bacterial chromosomes. Scientific reports 6 (2016) 23121.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of killing bacteria, comprising:
   treating the bacteria with a DNA condensation-inducing compound; and
   subsequently treating the bacteria with an Eis inhibitor.

2. The method of claim 1, wherein the DNA condensation-inducing compound is an antibiotic.

3. The method of claim 2, wherein the antibiotic is selected from the group consisting of: fusidic acid, nalidixic acid, linezolid, streptomycin, and rifampicin.

4. The method of claim 1, wherein the Eis inhibitor is a pyrrolo[1,5-a]pyrazine-based Eis inhibitor having the following structure:

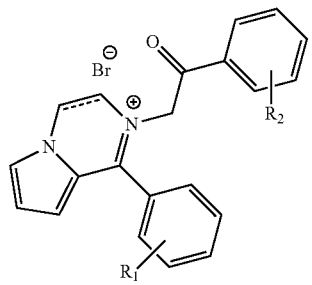

wherein $R_1$ is selected from the group consisting of H, p-F, and m,p-di-F; and wherein $R_2$ is selected from the group consisting of H, o-F, m-F, p-F, m-Cl, p-Cl, m-Br, p-Br, p Me, and m-OMe.

5. The method of claim 1, wherein the bacteria are mycobacteria.

6. The method of claim 1, wherein the bacteria include *Mycobacterium tuberculosis*.

7. The method of claim 1, wherein the bacteria include *Mycobacterium smegmatis*.

8. The method of claim 1, wherein the bacteria are causing an infection in a subject.

9. The method of claim 8, wherein the step of treating the bacteria with a DNA condensation-inducing compound includes administering the DNA condensation-inducing compound to the subject.

10. The method of claim 9, wherein the step of subsequently treating the bacteria with the Eis inhibitor includes administering the Eis inhibitor to the subject.

11. An antibiotic kit, comprising: a DNA condensation-inducing compound packaged together with an Eis inhibitor.

12. The kit of claim 11, wherein the DNA condensation-inducing compound is an antibiotic.

13. The kit of claim 12, wherein the antibiotic is selected from the group consisting of: fusidic acid, nalidixic acid, linezolid, streptomycin, and rifampicin.

14. The kit of claim 11, wherein the Eis inhibitor is a pyrrolo[1,5-a]pyrazine-based Eis inhibitor having the following structure:

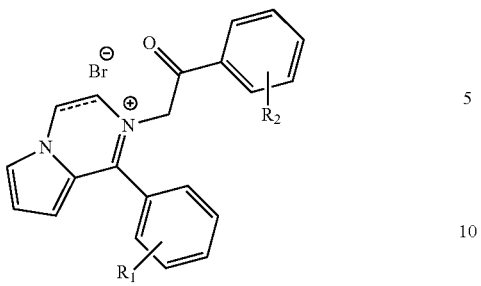

wherein R₁ is selected from the group consisting of H, p-F, and m,p-di-F; and wherein R₂ is selected from the group consisting of H, o-F, m-F, p-F, m-Cl, p-Cl, m-Br, p-Br, p Me, and m-OMe.

15. The kit of claim 11, further comprising instructions for killing bacteria.

16. The kit of claim 15, wherein the bacteria are mycobacteria.

17. The kit of claim 15, wherein the bacteria include *Mycobacterium tuberculosis*.

18. The kit of claim 15, wherein the bacteria include *Mycobacterium smegmatis*.

19. The kit of claim 15, wherein the bacteria are causing an infection in a subject.

20. The kit of claim 15, wherein the instructions comprise administering the DNA condensation-inducing compound to the subject, and subsequently administering the Eis inhibitor to the subject.

* * * * *